US010858707B2

(12) United States Patent
Schwartz et al.

(10) Patent No.: US 10,858,707 B2
(45) Date of Patent: Dec. 8, 2020

(54) METHODS AND COMPOSITIONS FOR RISK PREDICTION, DIAGNOSIS, PROGNOSIS, AND TREATMENT OF PULMONARY DISORDERS

(71) Applicant: National Jewish Health, Denver, CO (US)

(72) Inventors: David A. Schwartz, Aurora, CO (US); Max Seibold, Denver, CO (US)

(73) Assignee: NATIONAL JEWISH HEALTH, Denver, CO (US)

( * ) Notice: Subject to any disclaimer, the term of this patent is extended or adjusted under 35 U.S.C. 154(b) by 0 days.

(21) Appl. No.: 15/802,281

(22) Filed: Nov. 2, 2017

(65) Prior Publication Data

US 2019/0040467 A1 Feb. 7, 2019

Related U.S. Application Data

(63) Continuation of application No. 15/217,885, filed on Jul. 22, 2016, now abandoned, which is a continuation of application No. 14/171,536, filed on Feb. 3, 2014, now abandoned, which is a continuation of application No. 13/014,589, filed on Jan. 26, 2011, now Pat. No. 8,673,565.

(60) Provisional application No. 61/323,760, filed on Apr. 13, 2010, provisional application No. 61/323,238, filed on Apr. 12, 2010, provisional application No. 61/298,814, filed on Jan. 27, 2010, provisional application No. 61/298,473, filed on Jan. 26, 2010.

(51) Int. Cl.
*C12Q 1/6883* (2018.01)

(52) U.S. Cl.
CPC ...... *C12Q 1/6883* (2013.01); *C12Q 2600/118* (2013.01); *C12Q 2600/136* (2013.01); *C12Q 2600/156* (2013.01); *C12Q 2600/158* (2013.01); *C12Q 2600/172* (2013.01); *G01N 2333/4725* (2013.01); *G01N 2800/12* (2013.01)

(58) Field of Classification Search
None
See application file for complete search history.

(56) References Cited

U.S. PATENT DOCUMENTS

| | | | |
|---|---|---|---|
| 6,339,075 | B1 | 1/2002 | King et al. |
| 8,673,565 | B2 | 3/2014 | Schwartz et al. |
| 2002/0025520 | A1 | 2/2002 | Chee |
| 2002/0037538 | A1 | 3/2002 | Trepicchio et al. |
| 2003/0040009 | A1 | 2/2003 | Denny et al. |
| 2003/0092019 | A1 | 5/2003 | Meyer et al. |
| 2003/0096219 | A1 | 5/2003 | Wu et al. |
| 2004/0146890 | A1 | 7/2004 | Matsuzaki et al. |
| 2005/0125851 | A1 | 6/2005 | Whitsett et al. |
| 2007/0059783 | A1 | 3/2007 | Packer et al. |
| 2007/0099202 | A1 | 5/2007 | Young |
| 2007/0202109 | A1 | 8/2007 | Nakamura et al. |
| 2008/0195327 | A1 | 8/2008 | Young |
| 2010/0119474 | A1 | 5/2010 | Crystal et al. |
| 2012/0094842 | A1 | 4/2012 | Durie et al. |
| 2014/0220570 | A1 | 8/2014 | Schwartz et al. |
| 2017/0183730 | A1 | 6/2017 | Schwartz et al. |

FOREIGN PATENT DOCUMENTS

| | | |
|---|---|---|
| EP | 1403638 A1 | 3/2004 |
| JP | 2005328748 A | 12/2005 |
| WO | WO-2009/073167 A2 | 6/2009 |
| WO | WO-2009/140715 A1 | 11/2009 |
| WO | WO-2011/09434 A1 | 8/2011 |

OTHER PUBLICATIONS

Wise (Wise, Anastasia Leigh (2008). Unraveling the Etiology of Familial Interstitial Pneumonia: Genetic Investigations of a Complex Disease. Dissertation, Duke University. Retrieved from http://hdl.handle.net/10161/671).*
Syvanen (Nature Reviews Genetics Dec. 2001 vol. 2 pp. 930-942).*
Hui (Current Protocols in Human Genetics 2.10.1-2.10.8 Jan. 2008).*
Bouros (European Respiratory Journal vol. 26 No. 4 pp. 693-702).*
Moehle (J Mol Med 2006 vol. 84: 1055-1066).*
Gen Bank (dbSNP record rs41480348 added with build 127 on Dec. 1, 2006).*
Tabor (Nature Reviews Genetics May 2002 vol. 3 pp. 1-7).*
Balsamo, R. et al. (Jun. 2010). "Mucoactive drugs," *Eur Respir Rev* 19(116):127-133.
Borie, R. et al. (Aug. 5, 2013). "The MUC5B variant is associated with idiopathic pulmonary fibrosis but not with systemic sclerosis interstitial lung disease in the European Caucasian population," *PLoS One* 8(8):e70621.
Boucher, Richard C., "Idiopathic Pulmonary Fibrosis—A Sticky Business", *The New England Journal of Medicine* 2011, 364(16):1560-1561, 2 pages.
Burgel, Pierre-Regis et al.; "A morphometric study of mucins and small airway plugging in cystic fibrosis"; 2007, Thorax, vol. 62, pp. 153-161.
Caramori, G. et al. (Nov. 2004). "Mucin expression in peripheral airways of patients with chronic obstructive pulmonary disease," *Histopathology* 45(5):477-484.
Caramori, Gaetano et al.; "MUC5AC expression is increased in bronchial submucosal glands of stable COPD patients"; 2009, Histooatholooy, vol. 55, pp. 321-331.
Chan, Eric. Integrating Transcriptomics and Proteomics. G&P magazine 2006 vol. 6 No. 3 pp. 20-26.
Checa et al., "MMP-1 polymorphisms and the risk of idiopathic pulmonary fibrosis," Human Genetics, Springer, Berlin, DE, vol. 124, No. 5, Oct. 14, 2008 (Oct. 14, 2008), pp. 465-472.

(Continued)

*Primary Examiner* — Amanda Haney
(74) *Attorney, Agent, or Firm* — Mintz, Levin, Cohn, Ferris, Glovsky and Popeo, P.C.

(57) ABSTRACT

The invention provides diagnostic and therapeutic targets for pulmonary disease, in particular, fibrotic lung disease. The inventors have found that a genetic variant MUC5B gene is associated with increased expression of the gene, increased risk of developing a pulmonary disease, and an improved prognosis and survival among those developing the pulmonary disease.

19 Claims, 5 Drawing Sheets

Specification includes a Sequence Listing.

(56) References Cited

OTHER PUBLICATIONS

Chen, Y. et al. (Sep. 15, 2001). "In silico cloning of mouse Muc5b gene and upregulation of its expression in mouse asthma model," *Am J Respir Crit Care Med* 164(6):1059-1066.
Cosgrove et al., "The MUC5B Promoter Polymorphism Is Associated With a Less Severe Pathological Form of Familial Interstitial Pneumonia (FIP)," American Thoracic Society International Conference Abstracts C103. Pathogenesis, Biomarkers, and Risk Factors for Interstitial Lung Disease: From Bench to Bedside, May 18, 2012 (May 18, 2012), Retrieved from the Internet: URL: http://www.atsjournals.org/doi/abs/10.1164/ajrccm-conference.2012.185.1_MeetinqAbstracts.A6865.
DNA Sequencing by Capillary Electrophoresis, Applied Biosystems Chemistry Guide Second Edition 2009 pp. 1-310.
Helling et al., "A Common MUC5B Promoter Polymorphism (rs35705950) And Risk of Interstitial Lung Disease," American Thoracic Society International Conference Abstracts C19. Mucin Gene Regulation and Function: How Much Have We Learned? 2013, Retrieved from the Internet: URL: http://www.atsjournals.org/doi/abs/10.1164/ajrccm-conference.2013.187.1_MeetirngAbstracts.A3815.
Henke, M.O. et al. (Jul. 2004, e-published Feb. 26, 2004). "MUC5AC and MUC5B Mucins Are Decreased in Cystic Fibrosis Airway Secretions," *Am J Respir Cell Mol Biol* 31(1):86-91.
Henke, Markus et al.; "MUC5AC and MUC5B mucins increase in cystic fibrosis airway secretions during pulmonary exacerbation"; 2007, Am J Respir Crit Care Med, vol. 175, pp. 816-821.
Hill et al., "Functional Prostaglandin-Endoperoxide Synthase 2 Polymorphism Predicts Poor Outcome in Sarcoidosis," American Journal of Respiratory and Critical Care Medicine, vol. 174, No. 8, Oct. 15, 2006 (Oct. 15, 2006), pp. 915-922.
Hoshikawa, Yasushit et al. Hypoxia induces different genes in the lungs of rats compared with mice. Physical Genomics 2003 vol. 12 pp. 209-219.
Jiang, H.D. et al. (Jul. 2009, e-published Jun. 22, 2009). "MS80, a novel sulfated oligosaccharide, inhibits pulmonary fibrosis by targeting TGF-beta1 both in vitro and in vivo," *Acta Pharmacol Sin* 30(7):973-979.
Johnson et al., "Exploration of the MUC5B Polymorphism Frequency in Rheumatoid Arthritis Interstitial Lung Disease," American Thoracic Society International Conference Abstracts A42. Interstitial Lung Disease: Epidemiology, Evaluation and Pathogenesis, 2013, Retrieved from the Internet: URL: http://www.atsjournals.org/doi/abs/10.1164/ajrccm-conference.2013.187.1_MeetingAbstracts.A5982.
Jumblatt, M.M.et al. (Jan. 2003). "MUC7 expression in the human lacrimal gland and conjunctiva," *Cornea* 22(10):41-45.
Kadota, J et al. Long term efficacy and safety of clarithromycin treatment in patients with diffuse pandbronchiolitis. 2003 Repiratory Medicine vol. 97 pp. 844-850.
Kamio et al., "Direct determination of MUC5B promoter haplotypes based on the method of single-strand conformation polymorphism and their statistical estimation", Genomics, Academic Press, San Diego, US, vol. 84, No. 3, Sep. 1, 2004 (Sep. 1, 2004), pp. 613-622, XP004561108, ISSN: 0888-7543, DOI: 10.1016/J.YGENO.2004.05.008.
Kamio, Koichiro et al. Promoter Analysis and Aberrant Expression of the MUC5B gene in diffuse panbronchiolitis. Feb. 11, 2005 Am J Respir Crit Care Med vol. 171, No. 9, pp. 949-957.
Kesimer, Mehmet et al.; "Characterization of exosome-like vesicles released from human tracheobronchial ciliated epithelium: a possible role in innate defense"; 2009, FASEB, Journal, vol. 23, pp. 1858-1868.
Kim, C.H. et al. (Feb. 2010, e-published Nov. 27, 2009). "Expression of mucins in the mucosal surface of small intestines in 1 week-old pigs," *J Vet Med Sci* 72(2):245-247.
Mayo Clinic list of types of Interstital Lung disease. http://www.mayoclinic.org/interstitial-lung-disease/types.html accessed online Dec. 2, 2011.

Nguyen, Long P. et al.; "Chronic Exposure to Beta-Blockers Attenuates Inflammation and Mucin Content ina Murine Asthma Model"; 2008, American Journal of Respiratory Cell Mol. Biol., vol. 38, No. 3, pp. 256-262.
Peljto et al., "Risk Variant for ILD Does Not Influence Systemic Sclerosis (SSc) Associated ILD," American Thoracic Society International Conference Abstracts, D104. Connective Tissue Disease Related-Interstitial Lung Disease: Clinical Features and Treatment, May 18, 2012 (May 18, 2012), Retrieved from the Internet: URL: http://www.atsjournals.org/doi/abs/10.1164/ajrccm-conference.2012.185.1_MeetingAbstracts.A6605.
Peljto et al., "The Pulmonary Fibrosis-Associated MUC5B Promoter Polymorphism Does Not Influence the Development of Interstitial Penumonia in Systemic Sclerosis," Chest, vol. 142, No. 6, Dec. 2012 (Dec. 2012), pp. 1584-1588.
Pritchett, J.M. et al. (2012). "A MUC5B Promoter Polymorphism Is Associated with Increased Risk of IPF but not ALI or Lung Cancer," American Thoracic Society International Conference Abstracts C103. Pathogenesis, Biomarkers and Risk Factors for Interstitial Lung Disease: From Bench to Bedside, *American Journal of Respiratory and Critical Care Medicine* 185:A5164.
Rousseau, K et al Annals of Human Genetics 2007 vol. 71 pp. 561-569.
Rubin, Bruce K.; "Mucus structure and properties in cystic fibrosis"; 2007, Paediatr Respir Rev. vol. 8, pp. 4-7.
Seibold et al., "A Common MUC5B Promoter Polymorphism and Pulmonary Fibrosis," New England Journal of Medicine, vol. 364, No. 16, Apr. 21, 2011 (Apr. 21, 2011), pp. 1503-1512.
Stock et al., "A Mucin 5B (MUCSB) Promoter Polymorphism in Sarcoidosis," American Thoracic Society International Conference Abstracts A34. New Insights Into Sarcoidosis, May 18, 2012 (201205-18), Retrieved from the Internet: URL:http://www.atsjournals.org/doi/abs/10.1164/ajrccm-conference.2012.185.1_MeetingAbstracts.A135.
Stock et al., "Mucin 5B promoter polymorphism is associated with idiopathic pulmonary fibrosis but not with development of lung fibrosis in systemic sclerosis or sarcoidosis," Thorax, vol. 68, No. 5, Jan. 15, 2013 (Jan. 15, 2013), pp. 436-441.
Syvänen, A.C. (Dec. 2001). "Accessing genetic variation: genotyping single nucleotide polymorphisms," *Nat Rev Genet* 2(12):930-942.
Thai, Philip et al.; "Regulation of airway mucin gene expression"; 2008, Annu Rev Physiol, vol. 70, pp. 405-429.
Thornton, David J. et al.; "Structure and function of the polymeric mucins in airways mucus"; 2008, Annu Rev Physiol, vol. 70, pp. 459-486.
Tzortzaki, E.G. et al. (Aug. 2007, e-published Mar. 27, 2007). "Effects of antifibrotic agents on TGF-beta1, CTGF and IFN-gamma expression in patients with idiopathic pulmonary fibrosis," *Respir Med* 101(8):1821-1829.
Young, Hays W.J. et al.; "Central role of Muc5ac expression in mucous metaplasia and its regulation by conserved 5' elements"; 2007, Am J Respir Cell Mol Biol, vol. 37, pp. 273-290.
Whitehead, Andrew et al. Variation in tissue specific gene expression among natural populations. Genome Biology 2005 vol. 6 Issue 2 Article R13.
Zhang, Y. et al. (2011). "A Variant in the Promotor of MUC5B is Associated with Idiopathic Pulmonary Fibrosis and Not Chronic Obstructive Pulmonary Disease," American Thoracic Society International Conference Abstracts B102. Interstitial Lung Disease: Novel Management and Outcome Strategies, *American Journal of Respiratory and Critical Care Medicine* 183:A6395.
Zhang et al., "A Variant in the Promoter of MUCSB and Idiopathic Pulmonary Fibrosis," New England Journal of Medicine, vol. 364, No. 16, Apr. 21, 2011 (Apr. 21, 2011), pp. 1576-1577.
Search Report dated Jun. 19, 2013 in related European Patent Application No. 11737602.0, filed Jan. 26, 2011, 14 pages.
NCBI dbSNP database record for rs35705950 added with build 126 on May 4, 2006 found online at http://www.ncbi.nlm.nih.gov/projects/SNP/snp_ref.cgi?rs=35705950.
NCBI Assay ID record ss76902144 (submitted Oct. 1, 2007) found online at http://www.ncbi.nlm.nih.gov/projects/SNP/snp_ss.cgi?subsnp_id=76902144.

(56) References Cited

OTHER PUBLICATIONS

The Gene Card for MUC5B http://www.genecards.org/cqi-bin/carddisp.pl?gene=MUC5B&search=muc5b accessed online Dec. 2, 2011.

NCBI: Single Nucleotide Polymorphism. Cluster report: rs35705950; map; Jun. 16, 2005, NCBI SNP database {online] [retrived on Mar. 25, 2011] Retrived from the Internet: <URL: http://www.ncbi.nim.nih.gov/projects/SNP/snp ss.cgi?subsnp id=3866420>.

Search/Examination Report dated Jan. 26, 2011 from International Patent Application No. PCT/US2011/22621, 18 pages.

\* cited by examiner

METHODS AND COMPOSITIONS FOR RISK PREDICTION, DIAGNOSIS, PROGNOSIS, AND TREATMENT OF PULMONARY DISORDERS

CROSS-REFERENCES TO RELATED APPLICATIONS

This application is a continuation of U.S. application Ser. No. 15/217,885, filed Jul. 22, 2016, which is a continuation of U.S. application Ser. No. 14/171,536, filed Feb. 3, 2014, which is a continuation of U.S. application Ser. No. 13/014,589, now U.S. Pat. No. 8,673,565, filed Jan. 26, 2011, which claims priority to U.S. Provisional Application No. 61/298,473, filed Jan. 26, 2010, U.S. Provisional Application No. 61/298,814, filed Jan. 27, 2010, U.S. Provisional Application No. 61/323,238, filed Apr. 12, 2010, and U.S. Provisional Application No. 61/323,760, filed Apr. 13, 2010, the disclosures of which are incorporated herein in their entireties.

STATEMENT AS TO RIGHTS TO INVENTIONS MADE UNDER FEDERALLY SPONSORED RESEARCH AND DEVELOPMENT

The present invention was supported at least in part by government funding from the NIH Intramural Research Program of the National Inst. of Environmental Health Sciences (Grant No. Z01-ES101947) and the National Heart, Lung, and Blood Inst. (Grant Nos. U01-HL067467, R01-HL095393, R01-HL97163, P01-HL092870, and RC2-HL101715). The government has certain rights in the invention.

BACKGROUND OF THE INVENTION

Pulmonary fibrosis disorders are a growing concern in human and non-human populations. Pulmonary fibrosis is associated with a number of complex disorders (e.g., Herman-Pudlak Syndrome, tuberous sclerosis, neurofibromatosis, and dyskeratosis congenital). Idiopathic interstitial pneumonia (IIP) represents a class of chronic pulmonary fibrotic disorder characterized by progressive scarring of the alveolar interstitium leading to severe dyspnea, hypoxemia, and death. Idiopathic pulmonary fibrosis (IPF) is the most common type of IIP and currently has the highest mortality. Despite being an area of intensive research, the etiology of IPF is largely unknown. Familial clustering of IPF and differential susceptibility of individuals to fibrogenic dusts has implicated genetics in the development of this disorder. Genetic variants in the telomerase reverse transcriptase (TERT), surfactant protein A1, and surfactant protein C genes have been implicated in development of familial interstitial pneumonia (FIP). However, these mutations only account for a small percentage of FIP cases. Familial association with IPF is 5-20%, and inheritance appears to be autosomal. The efficacy of current treatments, such as fibrogenic agents, is variable, indicating a need for more individualized treatment.

Mucins represent a family of glycoproteins associated with mucosal epithelia. Mucins can be associated with the cell membrane or secreted, and typically form a component of mucus. Abnormal expression or mutations in these proteins have been associated with adenocarcinomas, as well as pulmonary disorders such as asthma and bronchitis.

The present inventors have found that genetic variants of the MUC5B gene are associated with pulmonary disease, and can provide a useful tool for prognosing the course of disease and determining a course of treatment. In addition, the increased level of MUC5B expression that results from the disclosed genetic variants provides a novel therapeutic target for pulmonary diseases such as IIP, IPF, and FIP.

BRIEF SUMMARY OF THE INVENTION

Accordingly, in some embodiments, the invention provides methods and compositions for diagnosis, risk prediction, and determining the course of pulmonary disease. The invention further provides personalized methods of treatment for pulmonary diseases.

In some embodiments, the invention provides methods of determining whether a subject has or is at risk of developing a pulmonary disease, said method comprising determining (detecting) whether a subject expresses an elevated MUC5B RNA level or an elevated MUC5B protein level relative to a standard (e.g., normal) control, wherein the presence of said elevated MUC5B RNA level or said elevated MUC5B protein level indicates said subject has or is at risk of developing a pulmonary disease. In some embodiments, the pulmonary disease is an interstitial lung disease, e.g., a fibrotic interstitial lung disease, such as idiopathic pulmonary fibrosis or familial interstitial pneumonia.

The level of MUC5B RNA or protein can be determined using an in vitro assay or in vivo imaging assay. In some embodiments, said elevated MUC5B protein level or said elevated MUC5B RNA level is determined from a biological sample from the subject, e.g., a pulmonary tissue or bodily fluid of said subject. The bodily fluid can be, e.g., whole blood, plasma, serum, urine, sputum, saliva, a bronchoalveolar lavage sample, or exhaled breath condensate. In some embodiments, the sample is further processed, e.g., to separate cellular components or subcellular components. For example, the determining can further comprises separating cells from the remaining sample, or isolating exosomes or subcellular vesicles.

In some embodiments, the method further comprises administering a treatment to the subject, e.g., a pulmonary disease treatment, or interstitial lung disease treatment. In some embodiments, the treatment is a mucolytic agent. In some embodiments, the treatment is a MUC5B antagonist. In some embodiments, the method further comprises determining a second MUC5B RNA level or MUC5B protein level after administering said treatment and comparing said second level to the level observed before administering said treatment.

In some embodiments, the expression level of at least one additional pulmonary disease marker is determined and compared to a standard control. For example, the at least one additional pulmonary disease marker can be selected from the group consisting of Surfactant Protein A, Surfactant Protein D, KL-6/MUC1, CC16, CK-19, Ca 19-9, SLX, MCP-1, MIP-1a, ITAC, glutathione, type III procollagen peptide, sIL-2R, ACE, neopterin, beta-glucuronidase, LDH, CCL-18, CCL-2, CXCL12, MMP7, and osteopontin. An aberrant expression level of the pulmonary disease marker indicates that the subject has or is at risk of developing a pulmonary disease. In some embodiments, the aberrant expression is elevated relative to a normal control. In some embodiments, the aberrant expression is reduced relative to a normal control. In some embodiments, the method comprises determining whether the genome of the subject comprises a genetic variant of the at least one additional pulmonary disease marker selected from the group consisting of Surfactant Protein A2, Surfactant Protein B, Surfactant Protein C, TERC, TERT, IL-1RN, IL-1α, IL-1β, TNF, Lymphotoxin α, TNF-RII, IL-10, IL-6, IL-12, IFNγ, TGFβ, CR1, ACE, IL-8, CXCR1, CXCR2, MUC1 (KL6), and MUC5AC, wherein the presence of a genetic variant of the at least one additional pulmonary disease marker is indicative that the subject has or is at risk of developing a pulmonary disease. In some embodiments, the method does not comprise determining whether the genome of the subject comprises a genetic variant of MUC5AC.

In some embodiments, the standard control is obtained from normal, non-diseased sample. In some embodiments, the standard control is from a different individual or pool of individuals. In some embodiments, the standard control is a standard obtained from a population of individuals that do not have a pulmonary disease. In some embodiments, the standard control is obtained from the same individual, e.g., obtained at a different time, e.g., prior to exposure to an airway stressor. Typically, when detecting or determining the expression level of a given RNA or protein (e.g., MUC5B), the same RNA or protein is detected in the standard control. However, in some embodiments, a different RNA or protein can be detected and the ratio used to determine whether the RNA or protein level from the subject is elevated. Moreover, in some embodiments, the method can comprise comparison to a positive control, e.g., from a known pulmonary disease sample, or a sample from a known individual or pool of individuals that carry a genetic variant MUC5B gene or have elevated MUC5B expression.

In some embodiments, the invention provides methods of determining whether a subject has or is at risk of developing a pulmonary disease, said method comprising detecting (determining) whether a genome of a subject comprises a genetic variant MUC5B gene, wherein the presence of said genetic variant MUC5B gene indicates said subject has or is at risk of developing a pulmonary disease. In some embodiments, the pulmonary disease is an interstitial lung disease, e.g., a fibrotic interstitial lung disease, such as idiopathic pulmonary fibrosis or familial interstitial pneumonia.

In some embodiments, the genetic variant MUC5B gene in said subject results in elevated expression of MUC5B RNA or MUC5B protein. In some embodiments, the subject is homozygous for said genetic variant MUC5B gene. In some embodiments, the subject is heterozygous for said genetic variant MUC5B gene. In some embodiments, the subject lacks the genetic variant MUC5B gene. In some embodiments, the genetic variant MUC5B gene is a genetic variant regulatory region MUC5B gene, e.g., a genetic variant promoter MUC5B gene. In some embodiments, the genetic variant MUC5B gene has a single nucleotide polymorphism (SNP). In some embodiments, the SNP is selected from the group consisting of single nucleotide polymorphism is rs2672792, rs72636989, MUC5B-Prm1, rs2672794, rs35705950, MUC5B-Prm2, rs11042491, rs2735726, rs868902, MUC5B-Prm3, MUC5B-Prm4, MUC5B-Prm5, rs868903, MUC5B-Prm6, rs885455, rs885454, MUC5B-Prm7, rs7115457, rs7118568 rs56235854 and rs2735738. In some embodiments, the presence of more than one SNP is determined. In some embodiments, the SNP is rs35705950.

In some embodiments, the genetic variant MUC5B gene comprises a first single nucleotide polymorphism (SNP) and a second SNP. In some embodiments, the first SNP is present within a first DNA strand and said second SNP is present within a second DNA strand. In some embodiments, the first and second SNP are present within the same DNA strand.

In some embodiments, the determining comprises use of at least one sequence selected from the group consisting of SEQ ID NOs:20-53 to determine whether the genome of the subject comprises a genetic variant MUC5B gene, e.g., by using an appropriate nucleic acid assay to detect the variant nucleotide in the selected sequence. For example, the determining can comprise use of one or more of the sequences of SEQ ID NOs:20-53 in an RT-PCR, array hybridization, or other appropriate SNP detection method as described herein. In some embodiments, the determining comprises (i) contacting a sample from the subject with a nucleic acid probe having at least 10 contiguous nucleotides of at least one of the sequences selected from SEQ ID NOs:20-53, or its complement, wherein said 10 contiguous nucleotides span the genetic variant nucleotide (i.e., the position of the SNP shown for each sequence), and (ii) determining whether the nucleic acid probe hybridizes to a nucleic acid in the sample. In some embodiments, the at least one sequence includes SEQ ID NO:24, wherein the presence of a T at position 28 of SEQ ID NO:24 indicates a genetic variant MUC5B gene, and that the subject has or will have an attenuated form of the pulmonary disease. The presence of a G at position 28 of SEQ ID NO:24 indicates that the subject has or will have a more severe form of the pulmonary disease (e.g., where the subject is homozygous for G at position 28, or lacking a genetic variant promoter MUC5B gene).

In some embodiments, the method further comprises determining whether said individual expresses an elevated MUC5B RNA level or an elevated MUC5B protein level relative to a standard control, wherein the presence of said elevated MUC5B RNA level or said elevated MUC5B protein level further indicates said subject has or is at risk of developing a pulmonary disease. Said step of determining can be carried out as discussed above.

In some embodiments, the method does not comprise determining whether the individual expresses an elevated level of MUC5AC RNA or protein. In some embodiments, the method does not comprise determining whether said individual expresses an elevated level of a second RNA or protein other than a MUC5B RNA or protein. In some embodiments, the method does not comprise determining whether said individual expresses an elevated level of a second RNA or protein other than a MUC5B RNA or protein, unless said second RNA or protein is a MUC5AC RNA or protein.

In some embodiments, the method further comprises administering a treatment to the subject, e.g., a pulmonary disease treatment, or interstitial lung disease treatment. In some embodiments, the treatment is a mucolytic agent. In some embodiments, the treatment is a MUC5B antagonist, e.g., small molecule that inhibits MUC5B production or activity. In some embodiments, the method further comprises determining a second MUC5B RNA level or MUC5B protein level after administering said treatment and comparing said second level to the level observed before administering said treatment.

In some embodiments, the method further comprises determining whether the genome of the subject comprises at least one additional genetic variant pulmonary disease marker gene. In some embodiments, the at least one additional pulmonary disease marker can be selected from the group consisting of Surfactant Protein A2, Surfactant Protein B, Surfactant Protein C, TERC, TERT, IL-1RN, IL-1α, IL-1β, TNF, Lymphotoxin α, TNF-RII, IL-10, IL-6, IL-12, IFNγ, TGFβ, CR1, ACE, IL-8, CXCR1, CXCR2, MUC1 (KL6), or MUC5AC. The presence of an additional genetic variant pulmonary disease marker gene can indicate that the subject is at risk of or has a pulmonary disease.

In some embodiments, the presence of the genetic variant MUC5B gene indicates that the subject has an attenuated form of the pulmonary disease. That is, the subject will have a reduced severity of symptoms, more gradual loss of lung function, or increased survival compared to the normal, non-attenuated form of the pulmonary disease, i.e., compared to the pulmonary disease as it occurs in an individual that does not have a genetic variant MUC5B gene.

Thus, in some embodiments, the invention provides methods of prognosing a pulmonary disease in a patient, said method comprising determining whether a genome of a subject comprises a genetic variant MUC5B gene, wherein the presence of said genetic variant MUC5B gene indicates an attenuated form of said pulmonary disease in said patient relative to the absence of said genetic variant MUC5B gene. The absence of a genetic variant MUC5B gene can indicate that the patient has a more aggressive form of said pulmonary disease. In some embodiments, the pulmonary disease is an interstitial lung disease, e.g., a fibrotic interstitial lung disease, such as idiopathic pulmonary fibrosis or familial interstitial pneumonia. Said genetic variant MUC5B gene can be as described above.

In some embodiments, the method further comprises setting a course of treatment for the subject, e.g., based on the presence of a genetic variant MUC5B gene in the subject. For example, the presence of a genetic variant MUC5B gene, or the level of MUC5B gene expression, can be determined in the subject, a treatment administered to the subject, and the progress of the subject monitored, e.g., by monitoring MUC5B expression over time or other pulmonary diagnostic indicators, and determining whether further treatment is necessary. Thus, in some embodiments, the method further comprises administering pulmonary disease treatment or an interstitial lung disease treatment to the subject. In some embodiments, the method further comprises determining whether the genome of the subject comprises a genetic variant MUC5B gene, wherein the presence of a genetic variant MUC5B gene indicates an attenuated form of said interstitial lung disease in said subject.

In some embodiments, the invention provides methods of determining whether a pulmonary disease is progressing in pulmonary disease patient, said method comprising: (i) determining a first level of MUC5B RNA or first level of MUC5B protein in said patient at a first time point; (ii) determining a second level of MUC5B RNA or second level of MUC5B protein in said patient at a second time point; and (iii) comparing the second level of MUC5B RNA to the first level of MUC5B RNA or comparing the second level of MUC5B protein to the first level of MUC5B protein, wherein if the second level of MUC5B RNA is greater than the first level of MUC5B RNA or if the first level of MUC5B protein is greater than the first level of MUC5B protein, the pulmonary disease is progressing in the patient. In some embodiments, the pulmonary disease is an interstitial lung disease, e.g., a fibrotic interstitial lung disease, such as idiopathic pulmonary fibrosis or familial interstitial pneumonia.

In some embodiments, the method further comprises determining the rate of progression based on said comparing. That is, an rapid increase in MUC5B expression in a short time is correlated with more rapid progression of the pulmonary disease. In some embodiments, said determining said first level of MUC5B RNA or first level of MUC5B protein and said second level of MUC5B RNA or second level of MUC5B protein comprises normalizing said first level of MUC5B RNA or first level of MUC5B protein and said second level of MUC5B RNA or second level of MUC5B protein to a level of RNA or protein expressed from a standard gene in said interstitial lung disease patient, e.g., GAPDH, beta-actin, HPRT1, beta-tubulin, or beta-20 microglobulin.

In some embodiments, the invention provides methods of treating, preventing, or ameliorating a pulmonary disease in a subject in need thereof, the method comprising administering to said patient an effective amount of a MUC5B antagonist, wherein said antagonist reduces the expression of the MUC5B gene or reduces the activity of the MUC5B protein as compared to the expression or activity in the absence of said MUC5B antagonist, thereby treating, preventing, or ameliorating the pulmonary disease in the subject. In some embodiments, the MUC5B antagonist is a nucleic acid, e.g., a pRNA, siRNA, or antisense sequence, and reduces expression of the MUC5B gene. In some embodiments, the MUC5B antagonist is a small molecule, e.g., that reduces translation of MUC5B mRNA or packaging or activity of the MUC5B protein. In some embodiments, the MUC5B antagonist is selected from the group consisting of: a MUC5B antibody or MUC5B-binding fragment thereof, a MUC5B-binding aptamer, and a mucolytic agent. In some embodiments, the MUC5B antagonist nucleic acid is capable of hybridizing to at least a 10-nucleotide contiguous sequence of a MUC5B encoding target nucleic acid sequence. In some embodiments, the method further comprises monitoring the subject, e.g., by determining the level of MUC5B RNA or protein before and after said administering, or at one or more time points, after said administering. Thus, in some embodiments, the method of treatment includes a step of determining whether the genome of the subject comprises a genetic variant MUC5B gene, and/or a step of determining whether the subject has an elevated level of MUC5B RNA or protein, as described herein.

In some embodiments, the invention provides methods of identifying a candidate pulmonary disease treatment compound, said method comprising: (i) contacting a test compound with a MUC5B protein; (ii) allowing said test compound to inhibit the activity of said MUC5B protein; and (iii) selecting the test compound that inhibits the activity of said MUC5B protein, thereby identifying a candidate pulmonary disease treatment compound. In some embodiments, the method is carried out in vivo, e.g., in an animal model for pulmonary disease. In some embodiments, the method is carried out in vitro.

In some embodiments, the invention provides methods of identifying a candidate pulmonary disease treatment compound, said method comprising: (i) contacting a test compound with a MUC5B secreting cell; (ii) allowing said test compound to inhibit secretion of MUC5B protein from said MUC5B secreting cell; and (iii) selecting the test compound that inhibits secretion of MUC5B protein from said MUC5B secreting cell, thereby identifying a candidate pulmonary disease treatment compound. In some embodiments, said MUC5B secreting cell is in vitro. In some embodiments, said MUC5B secreting cell forms part of a pulmonary tissue. In some embodiments, said pulmonary tissue forms part of an organism, i.e., the method is carried out in vivo. In some embodiments, the organism is a mammal, e.g., an animal model or a human.

The invention further provides kits, e.g., for determining whether a subject expresses an elevated level of MUC5B RNA or MUC5B protein, or carries a genetic variant MUC5B gene. In some embodiments, the kit comprises (a) a MUC5B binding agent capable of binding to a substance selected from the group consisting of (i) a genetic variant MUC5B gene sequence; (ii) a MUC5B RNA or fragment thereof; and (iii) a MUC5B protein or fragment thereof, and (b) a detecting reagent or a detecting apparatus capable of indicating binding of said MUC5B binding agent to said substance. In some embodiments, the MUC5B binding agent is labeled, e.g., with a fluorescent label or radioisotope. In some embodiments, the kit further comprises a sample collection device for collecting a sample from the subject. In some embodiments, the MUC5B binding agent binds a genetic variant MUC5B gene in the promoter region. In some embodiments, the kit further comprises at least one control sample, e.g., a non-variant MUC5B gene sequence or a sample from a normal, non-disease control.

DETAILED DESCRIPTION OF THE INVENTION

Figure 1:
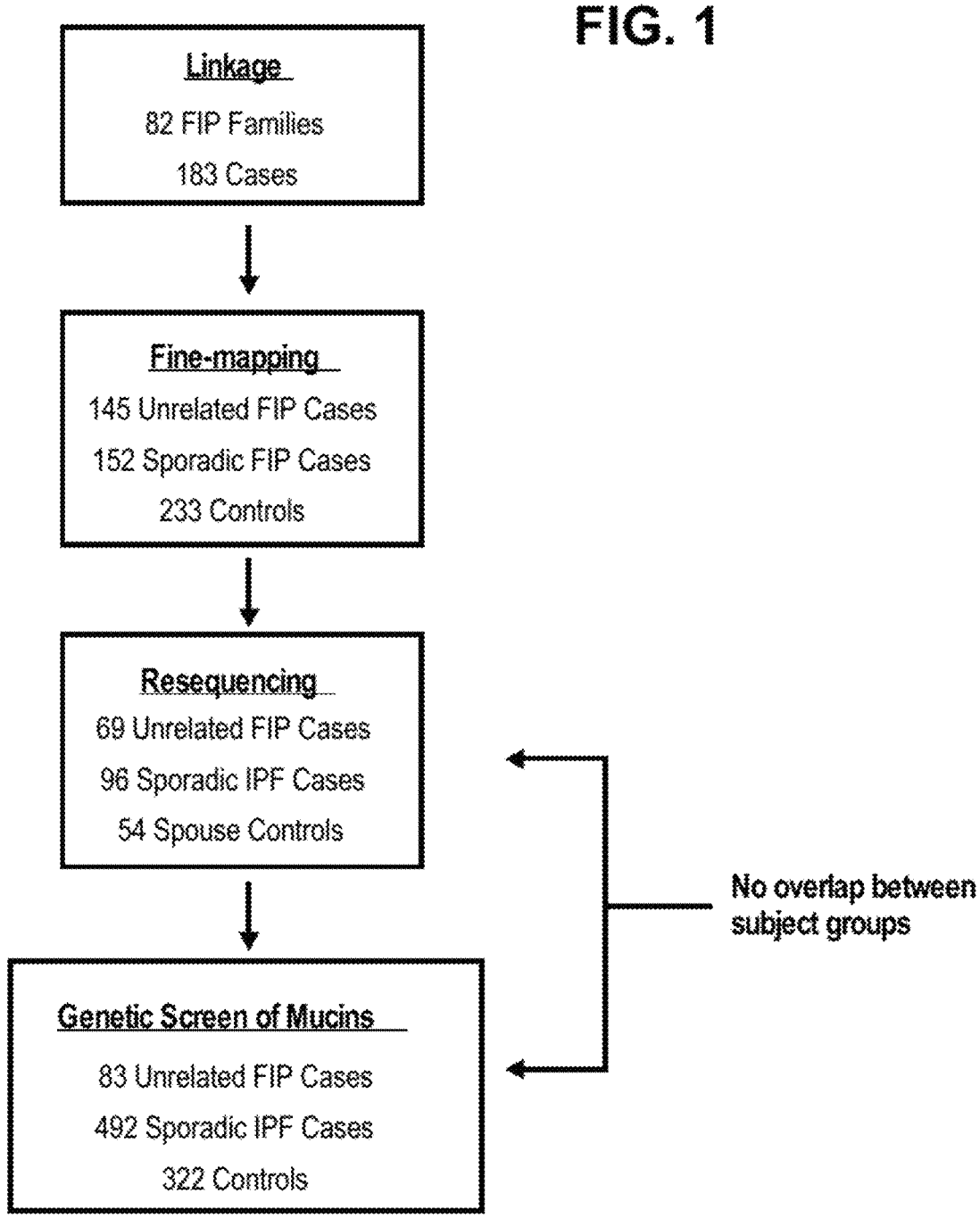
FIG. 1 represents a flow chart related to the genetic study design described herein.
Figure 2:
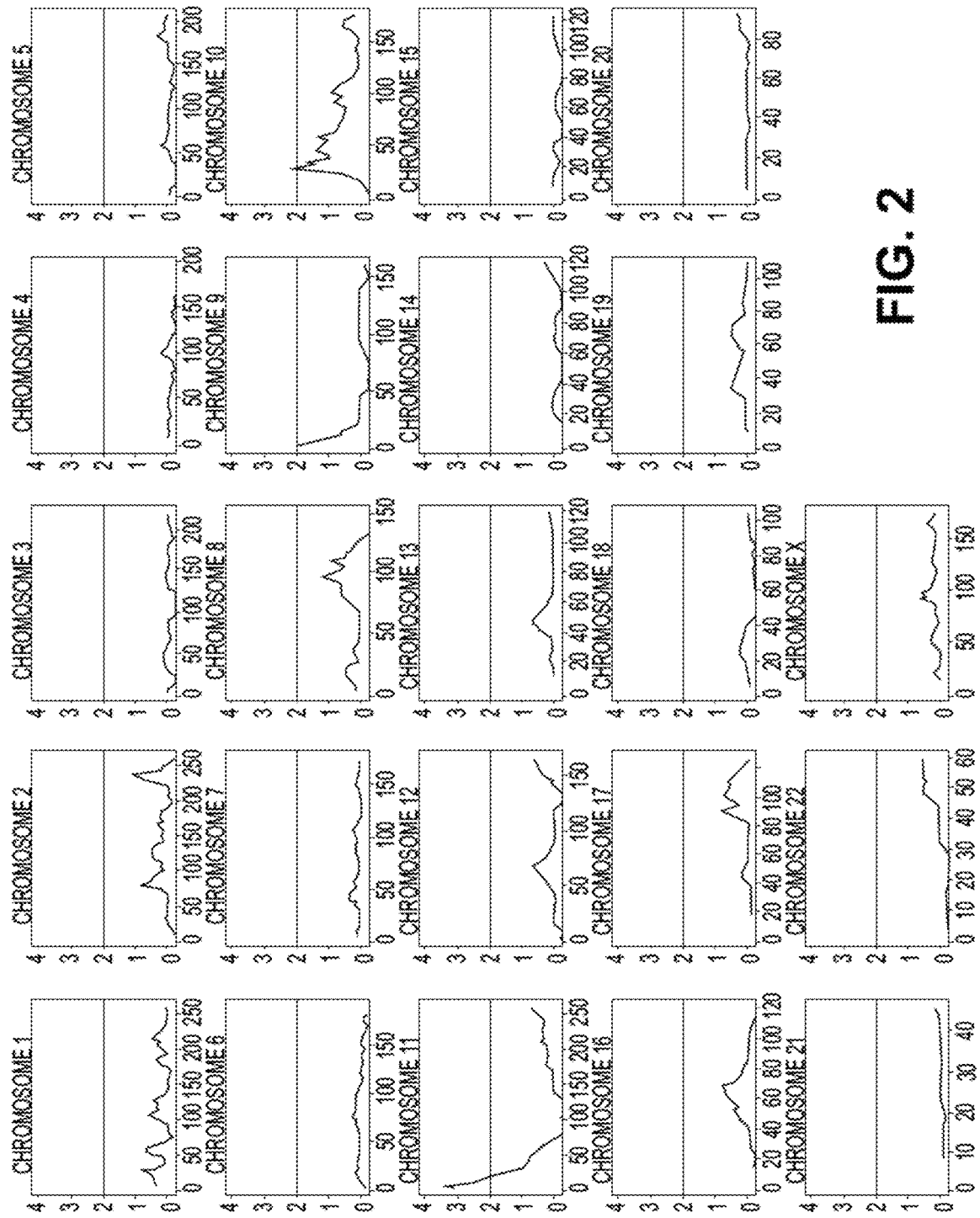
FIG. 2 represents a Multipoint LOD score graphs for whole genome screen (884 markers with an average inter-marker distance of 4.2 centimorgans (CM)) in 82 families with two or more cases of IIP.

The invention provides novel methods and compositions for diagnosing and predicting the severity of pulmonary disease, and a novel therapeutic target for ameliorating pulmonary disease. The inventors have found that individuals carrying genetic variants of the MUC5B gene that have elevated expression of the gene have an increased likelihood of developing a pulmonary disease, e.g., an interstitial lung disease such as fibrotic interstitial lung disease, idiopathic pulmonary fibrosis, familial interstitial pneumonia, etc. The presence of some genetic variations in the MUC5B gene, while increasing the likelihood of a pulmonary disease, are indicative of an attenuated form of the disease, e.g., a more gradual progression of symptoms and improved survival.

I. DEFINITIONS

The terms "pulmonary disease," "pulmonary disorder," "lung disease," etc. are used interchangeably herein. The term is used to broadly refer to lung disorders characterized by difficulty breathing, coughing, airway discomfort and inflammation, increased mucus, and/or pulmonary fibrosis.

Mucins are a family of high molecular weight, heavily glycosylated proteins (glycoproteins) produced by mammalian epithelia. Secreted, gel-forming mucins form a component of mucus. Typically, the N- and C-terminal ends of mucin proteins are lightly glycosylated, but rich in di-sulfide bond-forming cysteine residues.

Mucin 5b (MUC5B) is a gel-forming mucin expressed in airway epithelial tissue. Additional gel-forming mucins, MUC2, MUC5AC, and MUC6, have been mapped to the same chromosomal region on human chromosome 11. MUC5B is further characterized in Desseyn et al. (1996) *J. Biol. Chem.* 273:30157-64.

The term "genetic variant," in the context of a particular gene, refers a gene with a variant (e.g., non-standard or abnormal) nucleic acid sequence. The gene includes coding and non-coding sequences, such as regulatory regions. Genetic variants include mutations and polymorphic sequences. Thus, the genetic variant may affect the expression or activity of the gene or gene product. The genetic variant may be an insertion of one or more nucleotides, deletion of one or more nucleotides, or a substitution of one or more nucleotides. A single nucleotide polymorphism (SNP) is an example of a genetic variant.

The term "genetic variant MUC5B gene" refers to a MUC5B genetic variant (a MUC5B gene with a genetic variation as described above). The term "genetic variant promoter MUC5B gene" refers to a variation that is specifically in the promoter region of the MUC5B gene. Similarly, "genetic variant regulatory region MUC5B gene" and "genetic variant intronic MUC5B gene" localize the variation within the MUC5B gene. An example of a genetic variant MUC5B gene is rs35705950, which includes a SNP in the promoter region.

An "airway mucosal sample" can be obtained using methods known in the art, e.g., a bronchial epithelial brush as described herein. Additional methods include endobronchial biopsy, bronchial wash, bronchoalveolar lavage, whole lung lavage, transendoscopic biopsy, and transtracheal wash.

The terms "subject," "patient," "individual," etc. are not intended to be limiting and can be generally interchanged. That is, an individual described as a "patient" does not necessarily have a given disease, but may be merely seeking medical advice.

A "control" sample or value refers to a sample that serves as a reference, usually a known reference, for comparison to a test sample. For example, a test sample can be taken from a patient suspected of having a given pulmonary disease and compared to samples from a known pulmonary disease patient, known genetic variant MUC5B carrier, or a known normal (non-disease) individual. A control can also represent an average value gathered from a population of similar individuals, e.g., pulmonary disease patients or healthy individuals with a similar medical background, same age, weight, etc. A control value can also be obtained from the same individual, e.g., from an earlier-obtained sample, prior to disease, or prior to treatment. One of skill will recognize that controls can be designed for assessment of any number of parameters.

One of skill in the art will understand which controls are valuable in a given situation and be able to analyze data based on comparisons to control values. Controls are also valuable for determining the significance of data. For example, if values for a given parameter are widely variant in controls, variation in test samples will not be considered as significant.

As used herein, the terms "pharmaceutically" acceptable is used synonymously with physiologically acceptable and pharmacologically acceptable. A pharmaceutical composition will generally comprise agents for buffering and preservation in storage, and can include buffers and carriers for appropriate delivery, depending on the route of administration.

The terms "dose" and "dosage" are used interchangeably herein. A dose refers to the amount of active ingredient given to an individual at each administration. For the present invention, the dose will generally refer to the amount of pulmonary disease treatment, anti-inflammatory agent, or MUC5B antagonist. The dose will vary depending on a number of factors, including the range of normal doses for a given therapy, frequency of administration; size and tolerance of the individual; severity of the condition; risk of side effects; and the route of administration. One of skill will recognize that the dose can be modified depending on the above factors or based on therapeutic progress. The term "dosage form" refers to the particular format of the pharmaceutical, and depends on the route of administration. For example, a dosage form can be in a liquid form for nebulization, e.g., for inhalants, in a tablet or liquid, e.g., for oral delivery, or a saline solution, e.g., for injection.

As used herein, the terms "treat" and "prevent" are not intended to be absolute terms. Treatment can refer to any delay in onset, reduction in the frequency or severity of symptoms, amelioration of symptoms, improvement in patient comfort and/or respiratory function, etc. The effect of treatment can be compared to an individual or pool of individuals not receiving a given treatment, or to the same patient prior to, or after cessation of, treatment.

The term "prevent" refers to a decrease in the occurrence of pulmonary disease symptoms in a patient. As indicated above, the prevention may be complete (no detectable symptoms) or partial, such that fewer symptoms are observed than would likely occur absent treatment.

The term "therapeutically effective amount," as used herein, refers to that amount of the therapeutic agent sufficient to ameliorate the disorder, as described above. For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control.

The term "diagnosis" refers to a relative probability that a pulmonary disease is present in the subject. Similarly, the term "prognosis" refers to a relative probability that a certain future outcome may occur in the subject. For example, in the context of the present invention, prognosis can refer to the likelihood that an individual will develop a pulmonary disease, or the likely severity of the disease (e.g., severity of symptoms, rate of functional decline, survival, etc.). The terms are not intended to be absolute, as will be appreciated by any one of skill in the field of medical diagnostics.

The terms "correlating" and "associated," in reference to determination of a pulmonary disease risk factor, refers to comparing the presence or amount of the risk factor (e.g., dysregulation or genetic variation in a mucin gene) in an individual to its presence or amount in persons known to suffer from, or known to be at risk of, the pulmonary disease, or in persons known to be free of pulmonary disease, and assigning an increased or decreased probability of having/developing the pulmonary disease to an individual based on the assay result(s).

"Nucleic acid" or "oligonucleotide" or "polynucleotide" or grammatical equivalents used herein means at least two nucleotides covalently linked together. Oligonucleotides are typically from about 5, 6, 7, 8, 9, 10, 12, 15, 25, 30, 40, 50 or more nucleotides in length, up to about 100 nucleotides in length. Nucleic acids and polynucleotides are a polymers of any length, including longer lengths, e.g., 200, 300, 500, 1000, 2000, 3000, 5000, 7000, 10,000, etc. A nucleic acid of the present invention will generally contain phosphodiester bonds, although in some cases, nucleic acid analogs are included that may have alternate backbones, comprising, e.g., phosphoramidate, phosphorothioate, phosphorodithioate, or O-methylphophoroamidite linkages (see Eckstein, Oligonucleotides and Analogues: A Practical Approach, Oxford University Press); and peptide nucleic acid backbones and linkages. Other analog nucleic acids include those with positive backbones; non-ionic backbones, and non-ribose backbones, including those described in U.S. Pat. Nos. 5,235,033 and 5,034,506, and Chapters 6 and 7, ASC Symposium Series 580, *Carbohydrate Modifications in Antisense Research*, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made.

The terms "identical" or percent "identity," in the context of two or more nucleic acids (e.g., genomic sequences or subsequences, such as shown in SEQ ID NOs:20-53, or coding sequences) or polypeptide sequences, refer to two or more sequences or subsequences that are the same or have a specified percentage of amino acid residues or nucleotides that are the same (i.e., 50%, 55%, 60%, 65%, 70%, 75%, 80%, 85%, 90%, 91%, 92%, 93%, 94%, 95%, 96%, 97%, 98%, 99%, or more identity over a specified region), when compared and aligned for maximum correspondence over a comparison window, or designated region as measured using one of the following sequence comparison algorithms or by manual alignment and visual inspection. Such sequences are then said to be "substantially identical." This definition also refers to the compliment of a test sequence. Optionally, the identity exists over a region that is at least about 10 to about 100, about 20 to about 75, about 30 to about 50 amino acids or nucleotides in length.

An example of algorithms suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. As will be appreciated by one of skill in the art, the software for performing BLAST analyses is publicly available through the website of the National Center for Biotechnology Information (ncbi.nlm.nih.gov).

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymer.

The term "amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, e.g., an α carbon that is bound to a hydrogen, a carboxyl group, an amino group, and an R group, e.g., homoserine, norleucine, methionine sulfoxide, methionine methyl sulfonium. Such analogs may have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions similarly to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical or associated, e.g., naturally contiguous, sequences. Because of the degeneracy of the genetic code, a large number of functionally identical nucleic acids encode most proteins. For instance, the codons GCA, GCC, GCG and GCU all encode the amino acid alanine. Thus, at every position where an alanine is specified by a codon, the codon can be altered to another of the corresponding codons described without altering the encoded polypeptide. Such nucleic acid variations are "silent variations," which are one species of conservatively modified variations. Every nucleic acid sequence herein which encodes a polypeptide also describes silent variations of the nucleic acid. One of skill will recognize that in certain contexts each codon in a nucleic acid (except AUG, which is ordinarily the only codon for methionine, and TGG, which is ordinarily the only codon for tryptophan) can be modified to yield a functionally identical molecule. Accordingly, often silent variations of a nucleic acid which encodes a polypeptide is implicit in a described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention typically conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, *Proteins* (1984)).

A "label" or a "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins or other entities which can be made detectable, e.g., by incorporating a radiolabel into a peptide or antibody specifically reactive with a target peptide. Any method known in the art for conjugating an antibody to the label may be employed, e.g., using methods described in Hermanson, *Bioconjugate Techniques* 1996, Academic Press, Inc., San Diego.

A "labeled nucleic acid probe or oligonucleotide" is one that is bound, either covalently, through a linker or a chemical bond, or noncovalently, through ionic, van der Waals, electrostatic, or hydrogen bonds to a label such that the presence of the probe may be detected by detecting the presence of the label bound to the probe. Alternatively, method using high affinity interactions may achieve the same results where one of a pair of binding partners binds to the other, e.g., biotin, streptavidin.

The phrase "selectively (or specifically) hybridizes to" refers to the binding, duplexing, or hybridizing of a molecule only to a particular nucleotide sequence with a higher affinity, e.g., under more stringent conditions, than to other nucleotide sequences (e.g., total cellular or library DNA or RNA). One of skill in the art will appreciate that specific hybridization between nucleotides usually relies on Watson-Crick pair bonding between complementary nucleotide sequences.

The term "probe" or "primer", as used herein, is defined to be one or more nucleic acid fragments whose specific hybridization to a sample can be detected. A probe or primer can be of any length depending on the particular technique it will be used for. For example, PCR primers are generally between 10 and 40 nucleotides in length, while nucleic acid probes for, e.g., a Southern blot, can be more than a hundred nucleotides in length. The probe may be unlabeled or labeled as described below so that its binding to the target or sample can be detected. The probe can be produced from a source of nucleic acids from one or more particular (preselected) portions of a chromosome, e.g., one or more clones, an isolated whole chromosome or chromosome fragment, or a collection of polymerase chain reaction (PCR) amplification products. The length and complexity of the nucleic acid fixed onto the target element is not critical to the invention. One of skill can adjust these factors to provide optimum hybridization and signal production for a given hybridization procedure, and to provide the required resolution among different genes or genomic locations.

The probe may also be isolated nucleic acids immobilized on a solid surface (e.g., nitrocellulose, glass, quartz, fused silica slides), as in an array. In some embodiments, the probe may be a member of an array of nucleic acids as described, for instance, in WO 96/17958. Techniques capable of producing high density arrays can also be used for this purpose (see, e.g., Fodor (1991) Science 767-773; Johnston (1998) Curr. Biol. 8: R171-R174; Schummer (1997) Biotechniques 23: 1087-1092; Kern (1997) Biotechniques 23: 120-124; U.S. Pat. No. 5,143,854). One of skill will recognize that the precise sequence of the particular probes described herein can be modified to a certain degree to produce probes that are "substantially identical" to the disclosed probes, but retain the ability to specifically bind to (i.e., hybridize specifically to) the same targets or samples as the probe from which they were derived. Such modifications are specifically covered by reference to the individual probes described herein.

"Antibody" refers to a polypeptide comprising a framework region from an immunoglobulin gene or fragments thereof that specifically binds and recognizes an antigen, e.g., a specific bacterial antigen. Typically, the "variable region" contains the antigen-binding region of the antibody (or its functional equivalent) and is most critical in specificity and affinity of binding. See Paul, *Fundamental Immunology* (2003).

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies can exist as intact immunoglobulins or as any of a number of well-characterized fragments that include specific antigen-binding activity. Such fragments can be produced by digestion with various peptidases. Pepsin digests an antibody below the disulfide linkages in the hinge region to produce $F(ab)'_2$, a dimer of Fab which itself is a light chain joined to $V_H$-$C_H$1 by a disulfide bond. The $F(ab)'_2$ may be reduced under mild conditions to break the disulfide linkage in the hinge region, thereby converting the $F(ab)'_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990)).

II. MUCINS

There are several gel-forming mucins including, but not limited to, MUC6, MUC2, MUC5AC, and MUC5B. These proteins are large filamentous and highly 0-glycosylated.

III. PULMONARY DISEASES

The pulmonary diseases contemplated herein can include any pulmonary disorders, lung fibrosis diseases, interstitial lung diseases, idiopathic interstitial pneumonias (IIP), idiopathic pulmonary fibrosis, familial interstitial pneumonia (FIP), acute respiratory distress syndrome (ARDS), scleroderma lung disease, Sarcoidosis, Beryllium disease, rheumatoid arthritis associated lung disorder, collagen vascular associated lung disorder, cigarette smoke associated lung disorders, Sjögren's syndrome, mixed connective tissue disease, nonspecific interstitial pneumonitis (NSIP), etc.

Pulmonary fibrotic conditions, e.g., interstitial lung diseases (ILD) are characterized by shortness of breath, chronic coughing, fatigue and weakness, loss of appetite, and rapid weight loss. Pulmonary fibrosis is commonly linked to interstitial lung diseases (e.g., autoimmune disorders, viral infections or other microscopic injuries), but can be idiopathic. Fibrosis involves exchange of normal lung tissue with fibrotic tissue (scar tissue) that leads to reduced oxygen capacity.

Idiopathic interstitial pneumonias (IIP) are a subset of diffuse interstitial lung diseases of unknown etiology (the term "idiopathic" indicates unknown origin). IIPs are characterized by expansion of the interstitial compartment (i.e., that portion of the lung parenchyma sandwiched between the epithelial and endothelial basement membranes) with an infiltrate of inflammatory cells. The inflammatory infiltrate is sometimes accompanied by fibrosis, either in the form of abnormal collagen deposition or proliferation of fibroblasts capable of collagen synthesis.

Idiopathic Pulmonary Fibrosis (IPF) occurs in thousands of people worldwide with a doubling of prevalence over the past 10 years. Onset of IPF occurs around 50 to 70 years of age and starts with progressive shortness of breath and hypoxemia. IPF median survival is around 3-5 years and is to date untreatable. The etiology and pathogenesis of the condition is not well understood. About 5-20 percent of all cases of IPF have a family history and inheritance appears to be autosomal dominant.

Additional fibrotic pulmonary diseases include Acute Interstitial Pneumonia (AIP), Respiratory Bronchiolitis-associated Interstitial Lung Disease (RBILD), Desquamative Interstitial Pneumonia (DIP), Non-Specific Interstitial Pneumonia (NSIP), Bronchiolitis obliterans, with Organizing Pneumonia (BOOP).

AIP is a rapidly progressive and histologically distinct form of interstitial pneumonia. The pathological pattern is an organizing form of diffuse alveolar damage (DAD) that is also found in acute respiratory distress syndrome (ARDS) and other acute interstitial pneumonias of known causes (see *Clinical Atlas of Interstitial Lung Disease* (2006 ed.) pp 61-63).

RBILD is characterized by inflammatory lesions of the respiratory bronchioles in cigarette smokers. The histologic appearance of RBILD is characterized by the accumulation of pigmented macrophages within the respiratory bronchioles and the surrounding airspaces, variably, peribronchial fibrotic alveolar septal thickening, and minimal associated mural inflammation (see Wells et al. (2003) *Sem Respir. Crit. Care Med.* vol. 24).

DIP is a rare interstitial lung disease characterized by the accumulation of macrophages in large numbers in the alveolar spaces associated with interstitial inflammation and/or fibrosis. The macrophages frequently contain light brown pigment. Lymphoid nodules are common, as is a sparse but distinct eosinophil infiltrate. DIP is most common in smokers (see Tazelaar et al. (Sep. 21, 2010) *Histopathology*).

NSIP is characterized pathologically by uniform interstitial inflammation and fibrosis appearing over a short period of time. NSIP differs from other interstitial lung diseases in that it has a generally good prognosis. In addition, the temporal uniformity of the parenchymal changes seen in NSIP contrasts greatly with the temporal heterogeneity of usual interstitial pneumonia (see Coche et al. (2001) *Brit J Radiol* 74:189).

BOOP, unlike NSIP, can be fatal within days of first acute symptoms. It is characterized by rapid onset of acute respiratory distress syndrome; therefore, clinically, rapidly progressive BOOP can be indistinguishable from acute interstitial pneumonia. Histological features include clusters of mononuclear inflammatory cells that form granulation tissue and plug the distal airways and alveolar spaces. These plugs of granulation tissue may form polyps that migrate within the alveolar ducts or may be focally attached to the wall. (see White & Ruth-Saad (2007) *Crit. Care Nurse* 27:53).

Further details about the characteristics and therapies available for these diseases can be found, e.g., on the website of the American Lung Association at lungusa.org/lung-disease/pulmonary-fibrosis.

Diagnostic indicators of pulmonary disorders include biopsy (e.g., VATS or surgical lung biopsy), high resolution computed tomography (HRTC) or breathing metrics, such as forced expiratory volume (FEV1), vital capacity (VC), forced vital capacity (FVC), and FEV1/FVC.

Additional disorders associated with MUC5B expression and/or SNPs associated with MUC5B (e.g. SNP rs35705950) can include, but are not limited to, mucous secretion disorders, cancers (e.g. ovarian, breast lung, pancreatic etc.), eye disease, colitis, and cirrhosis of the liver.

IV. METHODS OF DIAGNOSIS AND PROGNOSIS

Methods for detecting and identifying nucleic acids and proteins and interactions between such molecules involve conventional molecular biology, microbiology, and recombinant DNA techniques within the skill of the art. Such techniques are explained fully in the literature (see, e.g., Sambrook, Fritsch & Maniatis, Molecular Cloning: A Laboratory Manual, Second Edition 1989, Cold Spring Harbor Laboratory Press, Cold Spring Harbor, N.Y.; Animal Cell Culture, R. I. Freshney, ed., 1986).

A. Biological Samples

For detection of a genetic variant using genomic DNA, a biological sample can be obtained from nearly any tissue. One of skill in the art will understand that a blood sample or a cheek swab is expected to carry the same genetic sequence information as a lung cell. For detection of a given expression level, pulmonary tissue samples and other biological fluids are typically used.

Biological samples can include a pulmonary mucosal sample or biological fluid such as blood or blood components (plasma, serum), sputum, mucus, urine, saliva, etc.

A pulmonary mucosal sample can be obtained using methods known in the art, e.g., a bronchial epithelial brush or exhaled breath condensate. Additional methods include bronchial biopsy, bronchial wash, bronchoalveolar lavage, whole lung lavage, transendoscopic biopsy, translaryngoscopic catheter, and transtracheal wash. A review of commonly used techniques, including comparisons and safety issues, is provided in Busse et al. (2005) *Am J Respir Crit Care Med* 172:807-816.

For lavage techniques, a bronchoscope can be inserted to the desired level of the airway. A small volume of sterile, physiologically acceptable fluid (e.g., buffered saline) is released, and immediately aspirated. The wash material contains cells from the mucosa and upper epithelia (Riise et al. (1996) *Eur Resp J* 9:1665).

For use of a bronchial epithelial brush, a sterile, non-irritating (e.g., nylon) cytology brush can be used. Multiple brushings can be taken to ensure representative sampling. The brush is then agitated in physiologically acceptable fluid, and the cells and debris separated using routine methods (Riise et al. (1992) *Eur Resp J* 5:382).

Cellular components can be isolated using methods known in the art, e.g., centrifugation. Similarly, subcellular components (e.g., exosomes or vesicles) can be isolated using known methods or commercial separation products (available from BioCat, System Bio, Bioscientific, etc.). An exemplary method is described e.g., by Thery et al. (2006) *Current Prot. Cell Biol.*

B. Detection of Genetic Variants

The inventors have found that genetic variations in the mucin genes are associated with pulmonary diseases. These genetic variations can be found in any part of the gene, e.g., in the regulatory regions, introns, or exons. Relevant genetic variations may also be found the intergene regions, e.g., in sequences between mucin genes. Insertions, substitutions, and deletions are included in genetic variants. Single nucleotide polymorphisms (SNPs) are exemplary genetic variants.

In particular, 14 independent SNPs are associated with pulmonary disorders (e.g. FIP or IPF). The studies disclosed herein demonstrate that presence of one or more of these SNPs associated with MUC5B can lead to predisposition to a pulmonary disorder. In addition, in some embodiments, if present, some of these SNPs are related to a transcription factor binding site. The transcription factor binding site can effect modulation of MUC5B expression, for example E2F3 loss, and HOXA9 and PAX-2 generation.

The invention thus provides methods for assessing the presence or absence of SNPs in a sample from a subject suspected of having or developing a pulmonary disorder (e.g., because of family history). In certain embodiments, one or more SNPs are screened in one or more samples, from a subject. The SNPs can be associated with one or more genes, e.g., one or more MUC genes or other genes associated with mucous secretion. In some embodiments, a MUC gene associated SNP is associated with MUC5B and/or another MUC gene, such as MUC5AC or MUC. SNPs contemplated for diagnostic, treatment, or prognosis can include SNPs found within a MUC gene and/or within a regulatory or promoter region associated with a MUC gene. For example, one or more SNPs can include, but are not limited to, detection of the SNPs of MUC5B shown in Table 4 (SEQ ID NOs:20-53), e.g., SNP rs35705950 (SEQ ID NO:24), alone or in combination with other genetic variations or SNPs and/or other diagnostic or prognostic methods.

Methods for detecting genetic variants such as a SNP are known in the art, e.g., Southern or Northern blot, nucleotide array, amplification methods, etc. Primers or probes are designed to hybridize to a target sequence. For example, genomic DNA can be screened for the presence of an identified genetic element of using a probe based upon one or more sequences, e.g., using a probe with substantial identity to a subsequence of the MUC5B gene, such as one of the subsequences shown in Table 4 (SEQ ID NOs: 20-53). Exemplary human MUC5B genomic sequences that can be used for reference and probe and primer design are found at GenBank Accession Nos. AF107890.1 and AJ004862.1. Expressed RNA can also be screened, but may not include all relevant genetic variations. Various degrees of stringency of hybridization may be employed in the assay. As the conditions for hybridization become more stringent, there must be a greater degree of complementarity between the probe and the target for duplex formation to occur. Thus, high stringency conditions are typically used for detecting a SNP.

Thus, in some embodiments, a genetic variant MUC5B gene in a subject is detected by contacting a nucleic acid in a sample from the subject with a probe having substantial identity to a subsequence of the MUC5B gene, and determining whether the nucleic acid indicates that the subject has a genetic variant MUC5B gene. In some cases, the sample can be processed prior to amplification, e.g., to separate genomic DNA from other sample components. In some cases, the probe has at least 90, 92, 94, 95, 96, 98, 99, or 100% identity to the MUC5B gene subsequence. Typically, the probe is between 10-500 nucleotides in length, e.g., 10-100, 10-40, 10-20, 20-100, 100-400, etc. In the case of detecting a SNP, the probe can be even shorter, e.g., 8-20 nucleotides in length. In some cases, the MUC5B gene sequence to be detected includes at least 8 contiguous nucleotides, e.g., at least 10, 15, 20, 25, 30, 35 or more contiguous nucleotides of one of the sequences shown in SEQ ID NOs:20-53. In some embodiments, the sequence to be detected includes 8 contiguous nucleotides, e.g., at least 10, 15, 20, 25, 30, 35 or more contiguous nucleotides of SEQ ID NO:24. In some aspects, the contiguous nucleotides include nucleotide 28 of SEQ ID NO:24.

The degree of stringency can be controlled by temperature, ionic strength, pH and/or the presence of a partially denaturing solvent such as formamide. For example, the stringency of hybridization is conveniently varied by changing the concentration of formamide within the range up to and about 50%. The degree of complementarity (sequence identity) required for detectable binding will vary in accordance with the stringency of the hybridization medium and/or wash medium. In certain embodiments, in particular for detection of a particular SNP, the degree of complementarity is about 100 percent. In other embodiments, sequence variations can result in <100% complementarity, <90% complimentarity probes, <80% complimentarity probes, etc., in particular, in a sequence that does not involve a SNP. In some examples, e.g., detection of species homologs, primers may be compensated for by reducing the stringency of the hybridization and/or wash medium.

High stringency conditions for nucleic acid hybridization are well known in the art. For example, conditions may comprise low salt and/or high temperature conditions, such as provided by about 0.02 M to about 0.15 M NaCl at temperatures of about 50° C. to about 70° C. Other exemplary conditions are disclosed in the following Examples. It is understood that the temperature and ionic strength of a desired stringency are determined in part by the length of the particular nucleic acid(s), the length and nucleotide content of the target sequence(s), the charge composition of the nucleic acid(s), and by the presence or concentration of formamide, tetramethylammonium chloride or other solvent(s) in a hybridization mixture. Nucleic acids can be completely complementary to a target sequence or exhibit one or more mismatches.

Nucleic acids of interest (e.g., nucleic acids comprising, or comprised within, SEQ ID NOs:20-53) can also be amplified using a variety of known amplification techniques. For instance, polymerase chain reaction (PCR) technology may be used to amplify target sequences (e.g., genetic variants) directly from DNA, RNA, or cDNA. In some embodiments, a stretch of nucleic acids is amplified using primers on either side of a targeted genetic variation, and the amplification product is then sequenced to detect the targeted genetic variation (using, e.g., Sanger sequencing, Pyrosequencing, Nextgen® sequencing technologies). For example, the primers can be designed to hybridize to either side of the upstream regulatory region of the MUC5B gene, and the intervening sequence determined to detect a SNP in the promoter region. In some embodiments, one of the primers can be designed to hybridize to the targeted genetic variant. In some cases, a genetic variant nucleotide can be identified using RT-PCR, e.g., using labeled nucleotide monomers. In this way, the identity of the nucleotide at a given position can be detected as it is added to the polymerizing nucleic acid. The Scorpion™ system is a commercially available example of this technology.

Thus, in some embodiments, a genetic variant MUC5B gene in a subject is detected by amplifying a nucleic acid in a sample from the subject to form an amplification product, and determining whether the amplification product indicates a genetic variant MUC5B gene. In some cases, the sample can be processed prior to amplification, e.g., to separate genomic DNA from other sample components. In some cases, amplifying comprises contacting the sample with amplification primers having substantial identity to MUC5B genomic subsequences, e.g., at least 90, 92, 94, 95, 96, 98, 99, or 100% identity. Typically, the sequence to be amplified is between 30-1000 nucleotides in length, e.g., 50-500, 50-400, 100-400, 50-200, 100-300, etc. In some cases, the sequence to be amplified or detected includes at least 8 contiguous nucleotides, e.g., at least 10, 15, 20, 25, 30, 35 or more contiguous nucleotides of one of the sequences shown in SEQ ID NOs:20-53. In some embodiments, the sequence to be amplified or detected includes 8 contiguous nucleotides, e.g., at least 10, 15, 20, 25, 30, 35 or more contiguous nucleotides of SEQ ID NO:24. In some aspects, the contiguous nucleotides include nucleotide 28 of SEQ ID NO:24.

Amplification techniques can also be useful for cloning nucleic acid sequences, to make nucleic acids to use as probes for detecting the presence of a target nucleic acid in samples, for nucleic acid sequencing, for control samples, or for other purposes. Probes and primers are also readily available from commercial sources, e.g., from Invitrogen, Clonetech, etc.

C. Detection of Expression Levels

Expression of a given gene, e.g., MUC5B or another mucin, pulmonary disease marker, or standard (control), is typically detected by detecting the amount of RNA (e.g., mRNA) or protein. Sample levels can be compared to a control level.

Methods for detecting RNA are largely cumulative with the nucleic acid detection assays described above. RNA to be detected can include mRNA. In some embodiments, a reverse transcriptase reaction is carried out and the targeted sequence is then amplified using standard PCR. Quantitative PCR (qPCR) or real time PCR (RT-PCR) is useful for determining relative expression levels, when compared to a control. Quantitative PCR techniques and platforms are known in the art, and commercially available (see, e.g., the qPCR Symposium website, available at qpcrsymposium.com). Nucleic acid arrays are also useful for detecting nucleic acid expression. Customizable arrays are available from, e.g., Affimatrix. An exemplary human MUC5B mRNA sequence, e.g., for probe and primer design, can be found at GenBank Accession No. AF086604.1.

Protein levels can be detected using antibodies or antibody fragments specific for that protein, natural ligands, small molecules, aptamers, etc. An exemplary human MUC5B sequence, e.g., for screening a targeting agent, can be found at UniProt Accession No. 000446.

Antibody based techniques are known in the art, and described, e.g., in Harlow & Lane (1988) *Antibodies: A Laboratory Manual* and Harlow (1998) *Using Antibodies: A Laboratory Manual*; Wild, *The Immunoassay Handbook*, 3d edition (2005) and Law, *Immunoassay: A Practical Guide* (1996). The assay can be directed to detection of a molecular target (e.g., protein or antigen), or a cell, tissue, biological sample, liquid sample or surface suspected of carrying an antibody or antibody target.

A non-exhaustive list of immunoassays includes: competitive and non-competitive formats, enzyme linked immunosorption assays (ELISA), microspot assays, Western blots, gel filtration and chromatography, immunochromatography, immunohistochemistry, flow cytometry or fluorescence activated cell sorting (FACS), microarrays, and more. Such techniques can also be used in situ, ex vivo, or in vivo, e.g., for diagnostic imaging.

Aptamers are nucleic acids that are designed to bind to a wide variety of targets in a non-Watson Crick manner. An aptamer can thus be used to detect or otherwise target nearly any molecule of interest, including a pulmonary disease associated protein. Methods of constructing and determining the binding characteristics of aptamers are well known in the art. For example, such techniques are described in U.S. Pat. Nos. 5,582,981, 5,595,877 and 5,637,459. Aptamers are typically at least 5 nucleotides, 10, 20, 30 or 40 nucleotides in length, and can be composed of modified nucleic acids to improve stability. Flanking sequences can be added for structural stability, e.g., to form 3-dimensional structures in the aptamer.

Protein detection agents described herein can also be used as a treatment and/or diagnosis of pulmonary disease or predictor of disease progression, e.g., propensity for survival, in a subject having or suspected of developing a pulmonary disorder. In certain embodiments, MUC5B antibodies can be used to assess MUC5B protein levels in a subject having or suspected of developing a pulmonary disorder. It is contemplated herein that antibodies or antibody fragments may be used to modulate MUC5B production in a subject having or suspected of developing a pulmonary disease. In certain embodiments, one or more agents capable of modulating MUC5B may be used to treat a subject having or suspected of developing a pulmonary disorder. One or more antibodies or antibody fragments may be generated to detect one or more of the SNPs disclosed herein by any method known in the art.

In certain embodiments, MUC5B diagnostic tests may include, but are not limited to, alone or in combination, analysis of rs35705950 SNP in MUC5B gene, MUC5B mRNA levels, and/or MUC5B protein levels.

D. Additional Pulmonary Disease Markers

The above methods of detection can be applied to additional pulmonary disease markers. That is, the expression level or presence of genetic variants of at least one additional pulmonary disease marker gene can be determined, or the activity of the marker protein can be determined, and compared to a standard control for the pulmonary disease marker. The examination of additional pulmonary disease markers can be used to confirm a diagnosis of pulmonary disease, monitor disease progression, or determine the efficacy of a course of treatment in a subject.

In some cases, pulmonary disease is indicated by an increased number of lymphocytes, e.g., CD4+CD28− cells (Moeller et al. (2009) *Am. J. Resp. Crit Care. Med.* 179:588; Gilani (2010) *PLoS One* 5:e8959).

Genetic variations in the following genes are associated with pulmonary disease: Surfactant Protein A2, Surfactant Protein B, Surfactant Protein C, TERC, TERT, IL-1RN, IL-1α, IL-1p, TNF, Lymphotoxin α, TNF-RII, IL-10, IL-6, IL-12, IFNγ, TGFβ, CR1, ACE, IL-8, CXCR1, CXCR2, MUC1 (KL6), or MUC5AC. Thus, the invention further includes methods of determining whether the genome of a subject comprises a genetic variant of at least one gene selected from these genes. The presence of a genetic variant indicates that the subject has or is at risk of developing pulmonary disease. Said determining can optionally be combined with determining whether the genome of the subject comprises a genetic variant MUC5B gene, or determining whether the subject has an elevated level of MUC5B RNA or protein to confirm or strengthen the diagnosis or prognosis.

Abnormal expression in the following genes can also be indicative of pulmonary disease: Surfactant Protein A, Surfactant Protein D, KL-6/MUC1, CC16, CK-19, Ca 19-9, SLX, MCP-1, MIP-1a, ITAC, glutathione, type III procollagen peptide, sIL-2R, ACE, neopterin, beta-glucuronidase, LDH, CCL-18, CCL-2, CXCL12, MMP7, and osteopontin. Thus, the expression of one of these genes can be detected and compared to a control, wherein an abnormal expression level indicates that the subject has or is at risk of developing pulmonary disease. Said determining can optionally be combined with determining whether the genome of the subject comprises a genetic variant MUC5B gene, or determining whether the subject has an elevated level of MUC5B RNA or protein to confirm or strengthen the diagnosis or prognosis.

E. Indications

The detection methods described herein can be used for diagnosis, prognosis, risk prediction, determining a course of treatment, monitoring therapeutic efficacy, and monitoring disease progression. One of skill will appreciate that each of the detection methods can be used alone or in combination.

For example, the presence of a genetic variant MUC5B gene can be determined in a subject suspected of having or at risk of developing a pulmonary disorder. In the event that a genetic variant MUC5B gene is observed, the subject can optionally undergo further testing, e.g., to determine the level of MUC5B gene expression, or detect a genetic variant form of at least one additional pulmonary disease marker. The subject can be prescribed a course of treatment based on the results of one or more tests. Such treatment can include administration of a MUC5B antagonist, or a standard pulmonary disease treatment such as a mucolytic drug. The expression level of the MUC5B gene can be detected again after treatment, or periodically during the course of treatment, to determine the therapeutic efficacy of the treatment. For example, if a pulmonary disease treatment is prescribed for periodic administration (e.g., daily, twice-daily, weekly, etc.), the MUC5B gene expression level can be monitored periodically thereafter (e.g., monthly).

The detection methods of the invention can be used to determine if the subject has an attenuated form of the pulmonary disease. The inventors have shown that individuals carrying the rs35705950 genetic variant MUC5B gene have a better pulmonary disease prognosis than individuals that do not carry a genetic variant MUC5B gene. Thus, determination of whether an individual carries the genetic variant MUC5B gene can be used to design a course of treatment for the individual.

V. METHODS OF TREATMENT

A. Pulmonary Disease Treatments

A number of pulmonary disease treatments are available for addressing airway inflammation and/or excess mucus secretion. These include agents that can be roughly categorized, e.g., as mucolytic agents, mucoregulatory agents, mucokinetic agents, and expectorants (see, e.g., Balsamo et al. (2010) Eur. Respir. Rev. 19:127-33), though there is some overlap in the categories. Such agents are useful for treating the pulmonary diseases described herein, e.g., as part of a course of treatment and monitoring, or after detection of elevated MUC5B RNA or protein, or detection of a genetic variant MUC5B gene.

Mucolytic drugs are those that decrease mucus viscosity, either by depolymerizing mucin glycoproteins or depolymerizing DNA and F-actin polymer networks. The first mode of action can be particularly useful for addressing excess MUC5B. Exemplary mucolytics include N-acetylcysteine, N-acystelyn, erdoseine, dornase alfa, thymosin beta4, dextran, pulmozyme, heparin, and bronchiotol (inhaled mannose).

Mucoregulators are those agents that regulate mucus secretion, or interfere with the DNA/F-actin network. Examples of mucoregulators include, e.g., carbocysteine, anticholoinergic agents, glucocorticoids, and macrolide antibiotics.

Mucokinetic agents increase mucus clearance by acting on the cilia lining the airway. Examplary mucokinetic agents include, e.g., bronchodilators, surfactants, and ambroxol.

Expectorants are agents that induce discharge of mucus from the airway or respiratory tract. Some examples include hypertonic saline, guaifenesin, dornase/pulmozyme, and bronchiotol (inhaled mannose).

The pulmonary disease treatment, such as the agents described above, can be used alone, sequentially, or in combination according to the methods described herein. In some embodiments, a pulmonary disease treatment is used in combination with a more targeted inhibitor of MUC5B expression.

B. MUC5B Antagonists

The results disclosed herein indicate that elevated expression of the MUC5B gene is associated with pulmonary disease. The invention thus includes methods and compositions for inhibiting the expression, secretion, and/or activity of MUC5B. Exemplary inhibitors include siRNA and antisense, pRNA (promoter-associated RNA, see, e.g., Schmitz et al. (2010) Genes Dev. 24:2264-69), MUC5B-specific antibodies and fragments thereof, and MUC5B-specific aptamers. In some embodiments, MUC5B activity can be inhibited or MUC5B clearance can be increased, e.g., using mucolytic agents, glycosylation inhibitors, or inhibitors of protein secretion. The terms "inhibitor" and "antagonist" and like terms are used synonymously herein.

Thus, a nucleotide sequence that specifically interferes with expression of the MUC5B gene at the transcriptional or translational level can be used to treat or prevent pulmonary disease. This approach may utilize, for example, siRNA and/or antisense oligonucleotides to block transcription or translation of a specific mRNA (e.g., a genetic variant RNA), either by inducing degradation of the mRNA with a siRNA or by masking the mRNA with an antisense nucleic acid. In some embodiments, the siRNA or antisense construct does not significantly block expression of other mucin genes.

Double stranded siRNA that corresponds to the MUC5B gene can be used to silence the transcription and/or translation by inducing degradation of MUC5B mRNA transcripts, and thus treat or prevent pulmonary disease (e.g., pulmonary disease associated with genetic variant MUC5B). The siRNA is typically about 5 to about 100 nucleotides in length, more typically about 10 to about 50 nucleotides in length, most typically about 15 to about 30 nucleotides in length. siRNA molecules and methods of generating them are described in, e.g., Bass, 2001, Nature, 411, 428-429; Elbashir et al., 2001, Nature, 411, 494-498; WO 00/44895; WO 01/36646; WO 99/32619; WO 00/01846; WO 01/29058; WO 99/07409; and WO 00/44914. A DNA molecule that transcribes dsRNA or siRNA (for instance, as a hairpin duplex) also provides RNAi. DNA molecules for transcribing dsRNA are disclosed in U.S. Pat. No. 6,573,099, and in U.S. Patent Application Publication Nos. 2002/0160393 and 2003/0027783, and Tuschl and Borkhardt, Molecular Interventions, 2:158 (2002). For example, dsRNA oligonucleotides that specifically hybridize to the MUC5B nucleic acid sequences described herein can be used in the methods of the present invention. A decrease in the severity of pulmonary disease symptoms in comparison to symptoms detected in the absence of the interfering RNA can be used to monitor the efficacy of the siRNA Antisense oligonucleotides that specifically hybridize to nucleic acid sequences encoding MUC5B polypeptides can also be used to silence transcription and/or translation, and thus treat or prevent pulmonary disease. For example, antisense oligonucleotides that specifically hybridize to a MUC5B polynucleotide sequence can be used. A decrease in the severity of pulmonary disease symptoms in comparison to symptoms detected in the absence of the antisense nucleic acids can be used to monitor the efficacy of the antisense nucleic acids.

Antisense nucleic acids are DNA or RNA molecules that are complementary to at least a portion of a specific mRNA molecule (see, e.g., Weintraub, Scientific American, 262:40 (1990)). Typically, synthetic antisense oligonucleotides are generally between 15 and 25 bases in length. Antisense nucleic acids may comprise naturally occurring nucleotides or modified nucleotides such as, e.g., phosphorothioate, methylphosphonate, and -anomeric sugar-phosphate, backbone-modified nucleotides.

In the cell, the antisense nucleic acids hybridize to the corresponding mRNA, forming a double-stranded molecule. The antisense nucleic acids, interfere with the translation of the mRNA, since the cell will not translate a mRNA that is double-stranded. Antisense oligomers of about 15 nucleotides are preferred, since they are easily synthesized and are less likely to cause problems than larger molecules when introduced into the target nucleotide mutant producing cell. The use of antisense methods to inhibit the in vitro translation of genes is well known in the art (Marcus-Sakura, Anal. Biochem., 172:289, (1988)). Less commonly, antisense molecules which bind directly to the DNA may be used.

siRNA and antisense can be delivered to the subject using any means known in the art, including by injection, inhalation, or oral ingestion. Another suitable delivery system is a colloidal dispersion system such as, for example, macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. Nucleic acids, including RNA and DNA within liposomes and be delivered to cells in a biologically active form (Fraley, et al., Trends Biochem. Sci., 6:77, 1981). Liposomes can be targeted to specific cell types or tissues using any means known in the art.

The invention also provides antibodies that specifically bind to MUC5B protein. Such antibodies can be used to sequester secreted MUC5B, e.g., to prevent gel-forming activity and formation of excess mucus.

An antibody that specifically detects MUC5B, and not other mucin proteins, can be isolated using standard techniques described herein. The protein sequences for MUC5B in a number of species, e.g., humans, non-human primates, rats, dogs, cats, horses, bovines, etc., are publically available.

Monoclonal antibodies are obtained by various techniques familiar to those skilled in the art. Briefly, spleen cells from an animal immunized with a desired antigen are immortalized, commonly by fusion with a myeloma cell (see, for example, Kohler & Milstein, Eur. J. Immunol. 6: 511-519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse et al., Science 246: 1275-1281 (1989).

Monoclonal antibodies are collected and titered against the MUC5B in an immunoassay, for example, a solid phase immunoassay with the immunogen immobilized on a solid support. Monoclonal antibodies will usually bind with a $K_d$ of at least about 0.1 mM, more usually at least about 1 M, and can often be designed to bind with a $K_d$ of 1 nM or less.

The immunoglobulins, including MUC5B-binding fragments and derivatives thereof, can be produced readily by a variety of recombinant DNA techniques, including by expression in transfected cells (e.g., immortalized eukaryotic cells, such as myeloma or hybridoma cells) or in mice, rats, rabbits, or other vertebrate capable of producing antibodies by well known methods. Suitable source cells for the DNA sequences and host cells for immunoglobulin expression and secretion can be obtained from a number of sources, such as the American Type Culture Collection (Catalogue of Cell Lines and Hybridomas, Fifth edition (1985) Rockville, Md.).

In some embodiments, the antibody is a humanized antibody, i.e., an antibody that retains the reactivity of a non-human antibody while being less immunogenic in humans. This can be achieved, for instance, by retaining the non-human CDR regions that are specific for MUC5B, and replacing the remaining parts of the antibody with their human counterparts. See, e.g., Morrison et al., PNAS USA, 81:6851-6855 (1984); Morrison and Oi, Adv. Immunol., 44:65-92 (1988); Verhoeyen et al., Science, 239:1534-1536 (1988); Padlan, Molec. Immun., 28:489-498 (1991); Padlan, Molec. Immun., 31(3):169-217 (1994). Techniques for humanizing antibodies are well known in the art and are described in e.g., U.S. Pat. Nos. 4,816,567; 5,530,101; 5,859,205; 5,585,089; 5,693,761; 5,693,762; 5,777,085; 6,180,370; 6,210,671; and 6,329,511; WO 87/02671; EP Patent Application 0173494; Jones et al. (1986) Nature 321:522; and Verhoyen et al. (1988) Science 239:1534. Humanized antibodies are further described in, e.g., Winter and Milstein (1991) Nature 349:293. For example, poly-nucleotides comprising a first sequence coding for humanized immunoglobulin framework regions and a second sequence set coding for the desired immunoglobulin complementarity determining regions can be produced synthetically or by combining appropriate cDNA and genomic DNA segments. Human constant region DNA sequences can be isolated in accordance with well known procedures from a variety of human cells.

The activity of MUC5B protein can be inhibited, or the clearance of MUC5B can be increased, using mucolytic agents that break up mucus and proteolyze mucins. Mucolytic agents are described herein. Additional inhibitors of MUC5B protein include glycosylation inhibitors and inhibitors of protein secretion from epithelial cells. An exemplary glycosylation inhibitor includes benzyl-O—N-acetyl-D galactosamine (specific for O-glycans) and. Additional inhibitors of protein glycosylation are disclosed, e.g., in Jacob (1995) Curr. Opin. Structural Biol. 5:605-11 and Patsos et al. 2005 Biochem Soc. Trans. 33:721-23. Secretion inhibitors include Brefeldin A, colchicine, and small molecules such as that disclosed in Stockwell (2006) Nat. Chem. Biol. 2:7-8. MUC5B activity can also be modulated by targeting the MARCKS protein (Adler et al. (2000) Chest 117: Supp 1 266S-267S).

C. Methods of Identifying MUC5B Antagonists

The invention further provides methods for identifying additional antagonists of MUC5B expression, secretion, and/or activity. Methods for screening for antagonists can involve measuring the ability of the potential antagonists to reduce an identifiable MUC5B activity or compete for binding with a known binding agent (e.g., MUC5B-specific antibody). For example, candidate agents can be screened for their ability to reduce MUC5B gel formation, reduce MUC5B secretion, reduce MUC5B glycosylation, etc.

The screening methods of the invention can be performed as in vitro or cell-based assays. Cell based assays can be performed in any cells in which MUC5B is expressed, either endogenously or through recombinant methods. Cell-based assays may involve whole cells or cell fractions containing MUC5B to screen for agent binding or modulation of MUC5B activity by the agent. Suitable cell-based assays are described in, e.g., DePaola et al., Annals of Biomedical Engineering 29: 1-9 (2001).

Agents that are initially identified as inhibiting MUC5B can be further tested to validate the apparent activity. Preferably such studies are conducted with suitable cell-based or animal models of pulmonary disease. The basic format of such methods involves administering a lead compound identified during an initial screen to an animal that serves as a model and then determining if in fact the pulmonary disease is ameliorated. The animal models utilized in validation studies generally are mammals of any kind. Specific examples of suitable animals include, but are not limited to, primates (e.g., chimpanzees, monkeys, and the like) and rodents (e.g., mice, rats, guinea pigs, rabbits, and the like).

The agents tested as potential antagonists of MUC5B can be any small chemical compound, or a biological entity, such as a polypeptide, sugar, nucleic acid or lipid. Alternatively, modulators can be genetically altered versions of MUC5B, e.g., forms that are not glycosylated. Essentially any chemical compound can be used as a potential modulator or ligand in the assays of the invention, although most often compounds that can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays).

In one embodiment, high throughput screening methods involve providing a combinatorial chemical or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487-493 (1991) and Houghton et al., *Nature* 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217-9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology*, 14(3):309-314 (1996) and PCT/US96/10287), carbohydrate libraries (see, e.g., Liang et al., *Science,* 274: 1520-1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506, 337; benzodiazepines, and U.S. Pat. No. 5,288,514).

D. Pharmaceutical Compositions

The compositions disclosed herein can be administered by any means known in the art. For example, compositions may include administration to a subject intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intrathecally, subcutaneously, subconjunctival, intravesicularlly, mucosally, intrapericardially, intraumbilically, intraocularly, orally, locally, by inhalation, by injection, by infusion, by continuous infusion, by localized perfusion, via a catheter, via a lavage, in a creme, or in a lipid composition. Administration can be local, e.g., to the pulmonary mucosa, or systemic.

Solutions of the active compounds as free base or pharmacologically acceptable salt can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations can contain a preservative to prevent the growth of microorganisms.

Pharmaceutical compositions can be delivered via intranasal or inhalable solutions or sprays, aerosols or inhalants. Nasal solutions can be aqueous solutions designed to be administered to the nasal passages in drops or sprays. Nasal solutions can be prepared so that they are similar in many respects to nasal secretions. Thus, the aqueous nasal solutions usually are isotonic and slightly buffered to maintain a pH of 5.5 to 6.5. In addition, antimicrobial preservatives, similar to those used in ophthalmic preparations, and appropriate drug stabilizers, if required, may be included in the formulation. Various commercial nasal preparations are known and can include, for example, antibiotics and antihistamines.

Oral formulations can include excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders. In some embodiments, oral pharmaceutical compositions will comprise an inert diluent or assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 75% of the weight of the unit, or preferably between 25-60%. The amount of active compounds in such compositions is such that a suitable dosage can be obtained For parenteral administration in an aqueous solution, for example, the solution should be suitably buffered and the liquid diluent first rendered isotonic with sufficient saline or glucose. Aqueous solutions, in particular, sterile aqueous media, are especially suitable for intravenous, intramuscular, subcutaneous and intraperitoneal administration. For example, one dosage could be dissolved in 1 ml of isotonic NaCl solution and either added to 1000 ml of hypodermoclysis fluid or injected at the proposed site of infusion Sterile injectable solutions can be prepared by incorporating the active compounds or constructs in the required amount in the appropriate solvent followed by filtered sterilization. Generally, dispersions are prepared by incorporating the various sterilized active ingredients into a sterile vehicle which contains the basic dispersion medium. Vacuum-drying and freeze-drying techniques, which yield a powder of the active ingredient plus any additional desired ingredients, can be used to prepare sterile powders for reconstitution of sterile injectable solutions. The preparation of more, or highly, concentrated solutions for direct injection is also contemplated. DMSO can be used as solvent for extremely rapid penetration, delivering high concentrations of the active agents to a small area.

E. Treatment Regimes

The invention provides methods of treating, preventing, and/or ameliorating a pulmonary disorder in a subject in need thereof, optionally based on the diagnostic and predictive methods described herein. The course of treatment is best determined on an individual basis depending on the particular characteristics of the subject and the type of treatment selected. The treatment, such as those disclosed herein, can be administered to the subject on a daily, twice daily, bi-weekly, monthly or any applicable basis that is therapeutically effective. The treatment can be administered alone or in combination with any other treatment disclosed herein or known in the art. The additional treatment can be administered simultaneously with the first treatment, at a different time, or on an entirely different therapeutic schedule (e.g., the first treatment can be daily, while the additional treatment is weekly).

Administration of a composition for ameliorating the pulmonary disease, e.g., by treating elevated expression of the MUC5B gene, can be a systemic or localized administration. For example, treating a subject having a pulmonary disorder can include administering an inhalable or intranasal form of anti-MUC5B agent (MUC5B antagonist) on a daily basis or otherwise regular schedule. In some embodiments, the treatment is only on an as-needed basis, e.g., upon appearance of pulmonary disease symptoms.

VI. KITS

The invention provides kits for detection of pulmonary disease markers in a subject. The kit can be for personal use or provided to medical professionals. The kit can be a kit for diagnosing or prognosing a pulmonary disorder, or for monitoring the progression of disease or the efficacy of treatment.

In some embodiments, the kit includes components for assessing MUC5B gene expression comprising, e.g., a nucleic acid capable of detecting MUC5B RNA or a MUC5B protein binding agent, optionally labeled. One of skill will appreciate that MUC5B gene expression can be determined by measuring MUC5B RNA or protein. The kit can further include assay containers (tubes), buffers, or enzymes necessary for carrying out the detection assay.

In some embodiments, the kit includes components for determining whether the genome of the subject carries a genetic variant MUC5B gene, e.g., a nucleic acid that specifically hybridizes to a genetic variant MUC5B gene sequence. Other components in a kit can include, DNA sequencing assay components, Taqman® genotyping assay components, Meta Analysis, one or more detection system(s), one or more control samples or a combination thereof. Kits can further include one or more agents where at least one of the agents is capable of associating with SNP rs35705950.

In some embodiments, the kit includes components to examine more than one pulmonary disease marker. For example, the kit can include marker detection agents, such as marker specific primers or probes attached to an addressable array. Exemplary markers include SNPs in the MUC5B genes, or genetic variants in other genes, e.g., Surfactant Protein A2, Surfactant Protein B, Surfactant Protein C, TERC, TERT, IL-1RN, IL-1α, IL-1β, TNF, Lymphotoxin α, TNF-RII, IL-10, IL-6, IL-12, IFNγ, TGFβ, CR1, ACE, IL-8, CXCR1 or CXCR2. In some embodiments, the expression level of the markers is detected instead of or in addition to the genetic sequence. In this case, useful pulmonary disease markers with aberrant expression include: Surfactant Protein A, Surfactant Protein D, KL-6/MUC1, CC16, CK-19, Ca 19-9, SLX, MCP-1, MIP-1a, ITAC, glutathione, type III procollagen peptide, sIL-2R, ACE, neopterin, beta-glucuronidase, LDH, CCL-18, CCL-2, CXCL12, MMP7, and osteopontin. Additional pulmonary disease markers can include the other MUC genes, e.g., MUC2, MUC5AC, and MUC6.

The kit will generally include at least one vial, test tube, flask, bottle, syringe or other container means, into which the testing agent, can be suitably reacted or aliquoted. Kits can also include components for comparing results such as a suitable control sample, for example a positive and/or negative control. The kit can also include a collection device for collecting and/or holding the sample from the subject. The collection device can include a sterile swab or needle (for collecting blood), and/or a sterile tube (e.g., for holding the swab or a bodily fluid sample).

The following discussion of the invention is for the purposes of illustration and description, and is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. All publications, patents, patent applications, Genbank numbers, and websites cited herein are hereby incorporated by reference in their entireties for all purposes.

VII. EXAMPLES

Example 1: Sequencing of Pulmonary, Gel-Forming Mucins and Disease Association

Study Populations:

Subjects with FIP or IPF were identified and phenotyped. The diagnosis of IP was established according to conventional criteria. Eligible subjects were at least 38 years of age and had IP symptoms for at least 3 months. A high resolution computerized tomography (HRCT) scan was required to show definite or probable IIP according to predefined criteria, and a surgical lung biopsy was obtained in 46% of affected subjects. FIP families were defined by the presence of two or more cases of definite or probable IIP within three degrees, with at least one case of IIP established as definite/probable IPF. Exclusion criteria included significant exposure to known fibrogenic agents or an alternative etiology for ILD. Control subjects for genetic analysis were acquired (FIG. 1).

Linkage Analysis:

A genome-wide linkage screen was completed in 82 multiplex families using a DeCode linkage panel consisting of a total of 884 markers with an average inter-marker distance of 4.2 CM. Multipoint non-parametric linkage analysis was performed using Merlin, previously described. Kong and Cox LOD scores were calculated using the $S_{pairs}$ statistic under an exponential model; support intervals were determined using the one-LOD-score-down method.

Fine-Mapping of Chromosome 11:

To interrogate the linked region on the p-terminus of chromosome 11 (8.4 Mb bounded by rs702966 and rs1136966), fine mapping by genotyping 306 tagging SNPs in 145 unrelated cases of FIP, 152 cases of IPF, and 233 Caucasian controls were performed. Tests of association comparing FIP cases and IPF cases to controls were calculated under an additive model for the minor allele.

Resequencing of MUC2 and MUC5AC:

Primer pairs to generate overlapping amplicons for resequencing the proximal promoter and most exons of MUC2 and MUC5AC were designed on sequences masked for repetitive elements, SNPs, and homology to other regions of the genome.

Genetic Screen of Lung-Expressed, Gel-Forming Mucins:

A case-control association study was conducted in an independent population of FIP (N=83), sporadic IPF (N=492), and control (N=322) subjects (Table 2) using tagging and other SNPs localized across the lung-expressed, gel-forming mucin genes on chromosome 11. 175 SNPs were successfully genotyped using the Sequenom iPlex assays, and haploview was used to test SNPs for allelic association with FIP and IPF. For those SNPs remaining significant after Bonferroni correction, odds ratios were estimated under an additive model for the rare allele after adjustment for age and gender via logistic regression. Chi-squared goodness-of-fit tests were computed to evaluate the evidence for disease-model explanations for genotypic departures from Hardy Weinberg Equilibrium (HWE) among cases. For the most highly-associated SNP, linkage and association modeling in pedigrees were used to test whether, in the original linkage families, the SNP was linked to the disease locus, was in linkage disequilibrium with the disease locus, and could account for the linkage signal.

Figure 3:
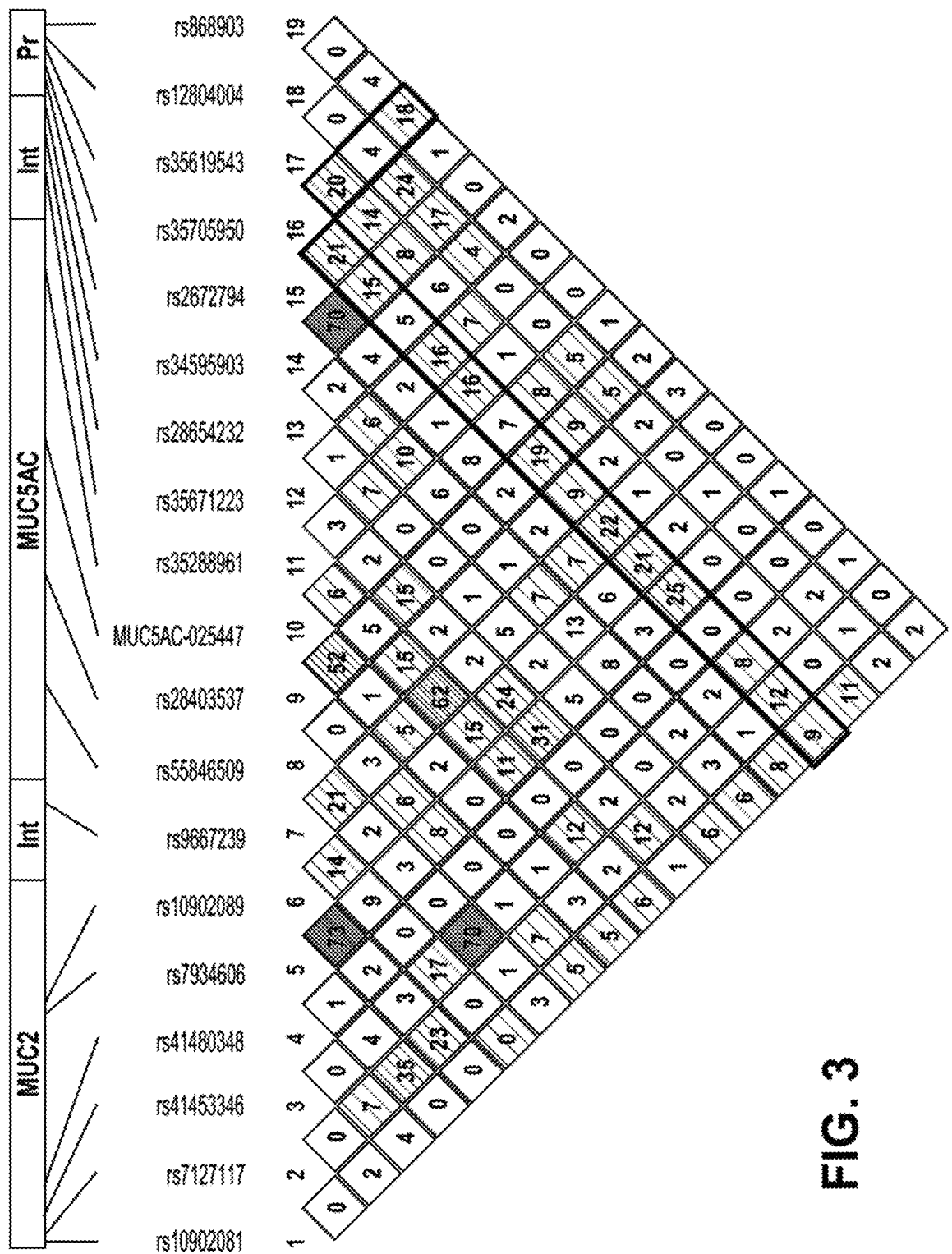
FIG. 3 illustrates pair-wise linkage disequilibrium (LD) plot for SNPs significantly associated with IPF or FIP by allelic association test in genetic screen of lung-expressed gel-forming mucins. LD values displayed are calculated by the r2 statistic for the mucin genetic screen IPF subjects (n=492). Multi-colored graphic about the plot indicates the approximate location of these SNPs within the gel-forming mucin region. The highly significant MUC5B promoter SNP (rs35705950) and the corresponding pairwise LD values are highlighted in red. Intergenic region is abbreviated as Int, and the MUC5B Promoter is abbreviated as Pr. LD patterns were qualitatively similar in the controls although in most instances the LD was weaker among controls.

Strong evidence for linkage based on the 82 FIP families occurred on chromosome 11 where the maximum multipoint LOD score was 3.3 (p=0.00004, D11S1318; FIG. 3). The 1-LOD support interval for this linked region was bounded by markers D11S4046 and D11S1760, spanning 3.4 Mb. Since D11S4046 was the most telomeric marker typed, the region of interest was inclusive of the p-terminus of chromosome 11. Within the 8.4 Mb larger region, 306 tagging SNPs were selected for fine-mapping in a case-control association analysis (145 FIP cases, 152 IPF cases, and 233 controls. Allelic association testing revealed 7 SNPs within the mucin 2 (MUC2) gene significantly associated with either FIP or IPF. MUC2 is contained in a genomic region harboring 4 gel-forming mucin genes (telomere to centromere: MUC6, MUC2, MUC5AC, and MUC5B). While there are reported recombination hotspots located between MUC6 and MUC2, and within the proximal portion of MUC5B, markers within MUC2 and MUC5AC exhibit strong linkage disequilibrium (LD) 17. Thus, MUC2 and MUC5AC were selected for resequencing using the oligonucleotide primers. Resequencing analysis identified 330 genetic variants in MUC2 and 195 genetic variants in MUC5AC. Allelic association testing between these genetic variants and disease status yielded 7 independent SNPs in both MUC2 and MUC5AC significantly associated with either FIP or IPF disease status.

We designed a genetic screen for common genetic variation across the genomic region containing the 3 gel-forming mucin genes expressed in the lung (MUC2, MUC5AC, and MUC5B) in an independent population of subjects with IIP (FIP=83 and IPF=492) and controls (n=322) (FIG. 1, Table 2). 19 independent SNPs were observed to be significantly associated by allelic test with either or both FIP or IPF after Bonferroni correction for multiple comparisons (Table 1). Of these 19 SNPs, 6 occurred in MUC2, one in the MUC2-MUC5AC intergenic region, 4 in MUC5AC, 3 in the MUC5AC-MUC5B intergenic region, and 5 in the putative MUC5B promoter, within 4 kb of the MUC5B transcription start site 18, 19 (Table 1).

Of significance, a SNP in the putative promoter of MUC5B, 3 kb upstream of the transcription start site (rs35705950) was found to have the most substantial effect on both FP and IPF. The minor allele of this SNP was present at a frequency of 33.8% in FIP cases, 37.5% in IPF cases, and 9.1% among controls (allelic association; FIP P=1.2× 10-15, IPF P=2.5×10-37). Notably, the genotype frequencies for rs35705950 were consistent with HWE in controls, but not among IPF cases (P=6.0×10-11) and nearly so among FIP cases (P=0.11). By comparing the genotype frequencies observed in cases and controls to those expected if rs35705950 is a true risk locus, the data demonstrates that these genotype frequencies are consistent with an additive genotypic effect on disease risk conferred by rs35705950 (P=0.88 and P=0.77, respectively for FIP and IPF to reject additive effect). In addition, the disease allele frequency and penetrance estimates suggest a similar disease model for both FIP and IPF. The odds ratio for disease for subjects heterozygous and homozygous for the rarer allele of this SNP were 6.8 (95% CI 3.9-12.0) and 20.8 (95% CI 3.8-113.7) for FIP, and 9.0 (95% CI 6.2-13.1) and 21.8 (95% CI 5.1-93.5) for IPF (Table 1). To ensure this SNP was not tagging another SNP in the MUC5B promoter region, the 4 kb region was resequenced upstream of the MUC5B transcription start site in 48 IPF cases and 48 controls (Table 3). It was observed that 34 genetic variants but none had a pairwise r2 LD value with rs35705950 above 0.2 (Table 4). Finally, among the original linkage families, rs35705950 was found to be both linked to (P=0.04) and in linkage disequilibrium with (P=1.5×10-9) the disease locus. While there is some evidence for other linked variants in the region (P=0.054), these results verify the relevance of this SNP to disease in these families.

TABLE 1

Genotypic association results assuming an additive model from the genetic screen of lung-expressed, gel-forming mucins in subjects with IIP (FIP = 83 and IPF = 492) and controls (n = 322).

| SNP | Nucleotide Amino Acid Change | Mucin Region | Hg19 Position | Minor Allele Frequency FIP (n = 83) | IPF (n = 492) | Controls (n = 322) | Genotypic Association Test by Disease Group Odds Ratio (95% CI) | P Value | Odds Ratio (95% CI) | P Value |
|---|---|---|---|---|---|---|---|---|---|---|
| rs10902081 | C/T | MUC2 Int7 | 1079809 | 37.2 | 38.6 | 47.9 | 0.6(0.4-0.9) | 0.011 | 0.7(0.5-0.8) | $4.3 \times 10^{-4}$ |
| rs7127117* | T/C | MUC2 Int7 | 1079879 | 49.3 | 60 | 47.4 | 1.0(0.7-1.5) | 0.826 | 1.6(1.3-2.0) | $6.9 \times 10^{-5}$ |
| rs41453346 | C/T Tyr426Tyr | MUC2 Ex10 | 1080894 | 5 | 6.5 | 2.2 | 1.9(0.8-4.3) | 0.124 | 2.8(1.6-5.2) | 0.001 |

TABLE 1-continued

Genotypic association results assuming an additive model from the genetic screen of lung-expressed, gel-forming mucins in subjects with IIP (FIP = 83 and IPF = 492) and controls (n = 322).

| SNP | Nucleotide Amino Acid Change | Mucin Region | Hg19 Position | Minor Allele Frequency | | | Genotypic Association Test by Disease Group | | | |
|---|---|---|---|---|---|---|---|---|---|---|
| | | | | FIP (n = 83) | IPF (n = 492) | Controls (n = 322) | Odds Ratio (95% CI) | P Value | Odds Ratio (95% CI) | P Value |
| rs41480348 | G/A Thr618Thr | MUC2 Ex15 | 1082605 | 8.4 | 6.5 | 12.1 | 0.7(0.4-1.2) | 0.188 | 0.5(0.4-0.8) | 0.001 |
| rs7934606* | C/T | MUC2 Int31 | 1093945 | 49.4 | 54 | 40.5 | 1.4(1.0-2.0) | 0.055 | 1.7(1.4-2.2) | $3.8 \times 10^{-6}$ |
| rs10902089* | A/G | MUC2 Int31 | 1094357 | 57.9 | 58.8 | 48.5 | 1.5(1.0-2.1) | 0.031 | 1.5(1.2-1.9) | $2.9 \times 10^{-4}$ |
| rs9667239 | C/T | MUC2-5AC Intergeric | 1143101 | 22.5 | 21 | 12.5 | 2.2(1.4-3.6) | 0.001 | 1.9(1.4-2.7) | $5.6 \times 10^{-5}$ |
| rs55846509 | G/A Arg47Gln | MUC5AC Ex2 | 1154294 | 3.1 | 5.5 | 1.6 | 1.7(0.6-5.1) | 0.316 | 3.6(1.7-7.3) | 0.001 |
| rs28403537 | C/T Ala497Val | MUC5AC Ex12 | 1161315 | 8.9 | 13 | 3.4 | 2.7(1.3-5.3) | 0.006 | 4.6(2.8-7.6) | $3.2 \times 10^{-9}$ |
| MUC5AC-025447* | C/T | MUC5AC Int26 | 826476** | 20.1 | 21 | 13.8 | 1.6(1.0-2.5) | 0.053 | 1.6(1.2-2.2) | 0.003 |
| rs35288961 | G/T | MUC5AC Int46 | 1220462 | 28.8 | 26.6 | 15.9 | 2.2(1.4-3.5) | $3.2 \times 10^{-4}$ | 2.0(1.5-2.6) | $3.7 \times 10^{-6}$ |
| rs35671223 | C/T | MUC5AC-5B Intergeric | 1227069 | 42.6 | 42.4 | 33.4 | 1.4(1.0-2.0) | 0.05 | 1.5(1.2-1.9) | 0.001 |
| rs28654232 | C/T | MUC5AC-5B Intergeric | 1229227 | 21.6 | 22.8 | 32.9 | 0.6(0.4-0.9) | 0.009 | 0.6(0.5-0.8) | $1.1 \times 10^{-4}$ |
| rs34595903* | C/T | MUC5AC-5B Intergeric | 1230393 | 21.5 | 23.3 | 34.8 | 0.5(3.3-0.7) | 0.001 | 0.5(0.4-0.7) | $2.4 \times 10^{-6}$ |
| rs2672794 | C/T | MUC5B Prm | 1241005 | 27.2 | 27.5 | 40.4 | 0.5(0.3-0.8) | 0.001 | 0.5(0.4-0.7) | $1.9 \times 10^{-7}$ |
| rs35705950 | G/T | MUC5B Prm | 1241221 | 33.8 | 37.5 | 9.1 | 6.2(3.7-10.4) | $3.7 \times 10^{-12}$ | 8.3(5.8-11.9) | $4.6 \times 10^{-3}$ |
| rs35619543* | G/T | MUC5B Prm | 1242250 | 40.3 | 39 | 23.8 | 2.4(1.6-3.6) | $3.3 \times 10^{-5}$ | 2.1(1.6-2.8) | $1.5 \times 10^{-8}$ |
| rs12804004 | G/T | MUC5B Prm | 1242299 | 39.2 | 39.4 | 48.9 | 0.6(0.4-0.9) | 0.019 | 0.6(0.5-0.8) | $1.2 \times 10^{-4}$ |
| rs868903* | T/C | MUC5B Prm | 1242690 | 65.4 | 61 | 49.5 | 1.8(1.3-2.6) | 0.001 | 1.6(1.3-2.1) | $2.8 \times 10^{-5}$ |

*For these SNPs, DNA was available for 304 controls.
**Nucleotide position based on NW_001838016.1.

TABLE 2

Demographic characteristics of subjects in the re-sequencing and mucin genetic screen analyses.

| | Re-Sequencing Subjects | | | Genetic Screen of Lung-expressed Gel-forming Mucins Subjects | | |
|---|---|---|---|---|---|---|
| | FIP | IPF | Control | FIP | IPF | Control |
| Number of subjects | 69 | 96 | 54 | 83 | 492 | 322* |
| Male gender | 41 (60%) | 61 (64%) | 18 (34%) | 44 (53.0%) | 352 (71.5%) | 147 (45.7%) |
| Caucasian | 68 (99%) | 89 (93%) | 53 (98%) | 83 (100%) | 492 (100%) | 322 (100%) |
| Age at diagnosis | 66 ± 10 | 65 ± 8 | 68 ± 8 | 66.3 ± 11.2 | 67.2 ± 8.1 | 60.3 ± 12.6 |
| Ever smoked | 44 (64%) | 71 (74%) | 25 (47%) | 46 (56.8%) | 342 (69.9%) | 245 (76.6%) |

*325 control subjects were included in allelic association analyses but only 322 in genotypic regression analyses as demographic variables needed for regression were missing for 3 subjects. Additionally, in some genotyping multiplexes for the lung-expressed gel forming mucins, 18 of the 322 controls were not screened due to lack of DNA availability

TABLE 3

Oligos used in resequencing of the MUC5B promoter

| MUC5B Promoter Amplicon | Forward Primer 5' > 3' | Reverse Primer 5' > 3' | Amplicon Size (bp) | Hg19 Coordinates |
|---|---|---|---|---|
| MUC5B-Prim-1 | GGTTCTCCTTGTCTTGCAGCCCCT (SEQ ID NO: 1) | ATGGGCTCTTGGTCTGCTCAGAG (SEQ ID NO: 2) | 616 | Chr11:1239997-1240612 |

TABLE 3-continued

Oligos used in resequencing of the MUC5B promoter

| MUC5B Promoter Amplicon | Forward Primer 5' > 3' | Reverse Primer 5' > 3' | Amplicon Size (bp) | Hg19 Coordinates |
|---|---|---|---|---|
| MUC5B-Prim-2 | GGGCCTGGCTCTGAGTACACATCCT (SEQ ID NO: 3) | AAGGAAAGGGACACAGCCGGTTCC (SEQ ID NO: 4) | 644 | Chr11:1240556-1241199 |
| MUC5B-Prim-3 | GGGTCCCCATTCATGGCAGGATT (SEQ ID NO: 5) | TTTCTCCATGGCAGAGCTGGGACC (SEQ ID NO: 6) | 601 | Chr11:1240957-1241557 |
| MUC5B-Prim-4 | CTAGTGGGAGGGACGAGGGCAAAGT (SEQ ID NO: 7) | CTCGTGGCTGTGACTGCACCCAG (SEQ ID NO: 8) | 610 | Chr11:1241386-1241995 |
| MUC5B-Prim-5 | TTGGCTAAGGTGGGAGACCT (SEQ ID NO: 9) | AGCTTGGGAATGTGAGAACG (SEQ ID NO: 10) | 700 | Chr11:1241791-1242490 |
| MUC5B-Prim-6 | CATGAGGGGTGACAGGTGGCAAA (SEQ ID NO: 11) | CCCGCGTTTGTCTTTCTGAAGTT (SEQ ID NO: 12) | 676 | Chr11:1242392-1243067 |
| MUC5B-Prim-7 | GGTCAGAAGCTTTGAAGATGGGC (SEQ ID NO: 13) | CTTGTCCAATGCCAGCCCTGATC (SEQ ID NO: 14) | 607 | Chr11:1242985-1243591 |
| MUC5B-Prim-8 | CTGCCAGGGTTAATGAGGAG (SEQ ID NO: 14) | GGATCAGGAAGGATTTGCAG (SEQ ID NO: 16) | 663 | Chr11:1243491-1244153 |
| MUC5B-Prim-9 | AGGCAGGCTGGCTGACCACTGTTT (SEQ ID NO: 17) | CGTGAAGACAGCATCGAGAGGGG (SEQ ID NO: 18) | 501 | Chr11:1243966-1244466 |
| MUC5B-Prim-5 Seq Pr. | TTGGCTAAGGTGGGAGACCT (SEQ ID NO: 19) | | | Chr11:1241791-1241810 |

TABLE 4

SNPs identified in resequencing of the MUC5B promoter

| Hg19 Position | SNP Name | Base Change | SEQ ID NO: | Flanking Sequence |
|---|---|---|---|---|
| 1240338 | rs2672792 | T/C | 20 | GTCACCTGCCCAGGTCCCCGAGGCC[T/C]GGAACACCTTCCTGCTGGGCCCACC |
| 1240485 | rs72636989 | G/A | 21 | CCACCCCAGGAGTTGGGGGGCCCCCGT[G/A]CCAGGGAGCAGGAGGCTGCCGAGG |
| 1240925 | Muc5B-Prm1 | C/T | 22 | GTGGCCCTGATCACTGGTGCCTGGA[C/T]GGCCTCTGAAGGGGTCTGTGGGGTC |
| 1241005 | rs2672794 | C/T | 23 | AACCCCCCTCGGGTTCTGTGTGGTC[C/T]AGGCCGCCCCTTTGTCTCCACTGCC |
| 1241221 | rs35705950 | G/T | 24 | TTTCTTCCTTTATCTTCTGTTTTCAGC[G/T]CCTTCAACTGTGAAGAAGTGA |
| 1241361 | MUC5B-Prm2 | A/G | 25 | TGCCCCGGACCCAGCCCAGTTCCCA[A/G]TGGGCCCTCTGCCCGGGGAGGTGC |
| 1241762 | MUC5B-Prm3 | C/T | 26 | GGTGGGCATCGGCTTGTGAGCTGGAGCCG[C/T]GGGCAGGGAGGGGGATGTCACGAG |
| 1241821 | rs11042491 | G/A | 27 | GGCTAAGGTGGGAGACCTGGGCGGGTGC[G/A]TCGGGGGACGTCTGCAGCAGAGGC |
| 1241848 | rs2735726 | T/C | 28 | TGCGTCGGGGGACGTCTGCAGCAGAGGCC[T/C]GGGCAGCAGGCACACCCCTCCTGCCAG |
| 1241993 | MUC5B-Prm4 | G/A | 29 | GGGGCCTGGGTGCAGTCACAGCCAC[G/A]AGCCCAGGGGTGGGGACTCTGGCC |
| 1242092 | MUC5B-Prm5 | C/T | 30 | CCCCTCCCACCGTGCCGTGCTGCAG[C/T]GGGTCTACCGGCCTGGATGTGAAA |
| 1242101 | MUC5B-Prm6 | C/T | 31 | CCGTGCCGTGCTGCAGCGGGTCTAC[C/T]GGCCTGGATGTGAAAGAGAGCTTG |
| 1242227 | rs11042646 | C/T | 32 | AGTCCCGGAAGTGAGCGGGGAGCTA[C/T]GCTGAGATCTGGGAGACCCCCTGC |
| 1242244 | rs55974837 | C/T | 33 | GGGAGCTACGCTGAGATCTGGGAGA[C/T]CCCCTGCCCCCACCCAGGTACAGG |
| 1242250 | rs35619543 | G/T | 34 | TACGCTGAGATCTGGGAGACCCCCT[G/T]CCCCCACCCAGGTACAGGGCCAGG |
| 1242299 | rs12804004 | T/G | 35 | GCAGAAGCCCGAGGTGTGCCCTGAG[T/G]TAAAGAAACCGTCACAAAGAACAA |
| 1242472 | rs56031419 | G/A | 36 | TGTCTCCGCCCTCCATCTCCAGAAC[G/A]TTCTCACATTCCCAAGCTGAAACC |
| 1242508 | rs868902 | C/A | 37 | CCCAAGCTGAAACCCTGTCCCCATG[C/A]AACACCAGCTCACCATCCCCTCTGCC |

TABLE 4-continued

SNPs identified in resequencing of the MUC5B promoter

| Hg19 Position | SNP Name | Base Change | SEQ ID NO: | Flanking Sequence |
|---|---|---|---|---|
| 1242567 | MUC5B-Prm7 | C/T | 38 | GGCGCCCACCGTCCACACTCCGTCT[C/T]TGCGGGTTTCATGACTCCAGGGGCAG |
| 1242599 | MUC5B-Prm8 | G/A | 39 | TTTCATGACTCCAGGGGCAGCACAC[G/A]AGTGGCCCCTCCTGCCTTTGTCCTC |
| 1242607 | MUC5B-Prm9 | C/T | 40 | CTCCAGGGGCAGCACACGAGTGGCC[C/T]CTCCTGCCTTTGTCCTCTGTGTCCA |
| 1242690 | rs868903 | C/T | 41 | CCCCCATGGAGCAGCCTGGGCCAGCC[C/T]CTCCTTTTCACGGCTGAACCGTAT |
| 1242910 | MUC5B-Prm10 | G/A | 42 | ACCCCCACCAGCAGGGCACAGGGCTCC[G/A]GGTCCCCACGTCTCTGCCAACACTT |
| 1242977 | MUC5B-Prm11 | G/A | 43 | CTTGATCCCCGCCATCCTATTGAGC[G/A]TGAGACAGGTCAGAAGCTTTGAAG |
| 1243218 | MUC5B-Prm12 | G/A | 44 | GTCTGCGCCACGGAGCATTCAGGAC[G/A]CTGGTGACCAGGGAGCCAGGAGGT |
| 1243378 | rs885455 | A/G | 45 | CGTCAAGGAGGTTTACCACATAGCCCCC[A/G]GGAAGCCCACCCGACACCAGCCGGA |
| 1243391 | rs885454 | G/A | 46 | TTTACCACATAGCCCCCRGGAAGCCCACCC[G/A]ACACCAGCCGGAGGTGCTAGGCTTC |
| 1243409 | MUC5B-Prm13 | T/C | 47 | CCCACCCGACACCAGCCGGAGGTGC[T/C]AGGCTTCTGCGGCTCCCACCTGGG |
| 1243911 | MUC5B-Prm14 | G/A | 48 | GGACCCATGGTCAGTGGCTGGGGGT[G/A]CTGCCCAGAGGCTGGGATTCCCTTC |
| 1244060 | rs7115457 | G/A | 49 | GCCATCTAGGACGGGTGCCAGGTGG[G/A]GTAGGCCCTTCTCTCCCTTCCGATT |
| 1244080 | rs7118568 | C/G | 50 | GGTGGGGTAGGCCCTTCTCTCCCTT[C/G]CGATTCTCAGAAGCTGCTGGGGGTG |
| 1244197 | rs56235854 | G/A | 51 | AGCCCCTCCCCGAGAGCAAACACAC[G/A]TGGCTGGAGCGGGAAGAGCATGGTGC |
| 1244219 | rs2735738 | T/C | 52 | CACGTGGCTGGAGCGGGAAGAGCA[T/C]GGTGCCCTGCGTGGCCTGGCCTGGC |
| 1244438 | MUC5B-Prm15 | C/T | 53 | GCCGCAGGCAGGTAAGAGCCCCCCA[C/T]TCCGCCCCCTCTCGATGCTGTCTT |

Next, the relationship between the rs35705950 SNP and the 18 other SNPs significantly associated with P were analyzed. Testing pairwise LD between these SNPs by the r2 statistic, 10 of the 18 SNPs were found to exhibit low level LD (r2=0.15-0.27) with rs35705950 among IPF cases, suggesting the significance of these SNPs is due to LD with rs35705950 (FIG. 3). Using genotypic logistic regression models to adjust for rs35705950 effects, we observed that the coefficients and corresponding P values were substantially reduced for all 18 SNPs which were previously associated with FIP and/or IPF (Table 5). After controlling for rs35705950, only one SNP retained nominal significance for IPF (rs41480348, P=0.04). It was demonstrated that the significance of the rs35705950 SNP was largely unaffected by adjustment for any of the 18 SNPs tested (P value for all SNP models was less than $1.7 \times 10^{-9}$ for FIP and $1.1 \times 10^{-24}$ for IPF; Table 5). These results demonstrate a strong independent effect of the rs3570590 SNP on both FIP and IPF.

TABLE 5

Genotypic logistic regression models for the 19 significant SNPs in the screen of lung-expressed gel-forming mucins alone, and after adjusting for rs35705950, in patients with IPF or FIP.

| | | IPF Single SNP Model | | IPF rs35705950 | | FIP Single SNP Model | | FIP rs35705950 | |
|---|---|---|---|---|---|---|---|---|---|
| Model # | SNP | Odds Ratio (95% C.I) | P Value | Odds Ratio (95% C.I) | P Value | Odds Ratio (95% C.I) | P Value | Odds Ratio (95% C.I) | P Value |
| 1 | rs10902081 | 0.7 (0.5-0.8) | $4.3 \times 10^{-4}$ | 0.9 (0.7-1.2) | 0.429 | 0.6 (0.4-0.9) | 0.011 | 0.8 (0.5-1.2) | 0.25 |
| | rs35705950 | x | x | 8.3 (5.7-11.9) | $1.5 \times 10^{-29}$ | x | x | 5.9 (3.5-10.1) | $6.6 \times 10^{-11}$ |
| 2 | rs7127117 | 1.6 (1.3-2.0) | $6.9 \times 10^{-5}$ | 1.1 (0.8-1.4) | 0.509 | 1.0 (0.7-1.5) | 0.826 | 0.7 (0.4-1.1) | 0.094 |
| | rs35705950 | x | x | 7.9 (5.4-11.6) | $1.3 \times 10^{-25}$ | x | x | 6.3 (3.5-11.4) | $7.3 \times 10^{-10}$ |
| 3 | rs41453346 | 2.8 (1.6-5.2) | 0.001 | 1.1 (0.6-2.2) | 0.72 | 1.9 (0.8-4.3) | 0.124 | 1.2 (0.5-3.0) | 0.653 |
| | rs35705950 | x | x | 8.1 (5.6-11.8) | $2.7 \times 10^{-28}$ | x | x | 6.1 (3.6-10.3) | $1.2 \times 10^{-11}$ |
| 4 | rs41480348 | 0.5 (0.4-0.8) | 0.001 | 0.6 (0.4-1.0) | 0.04 | 0.7 (0.4-1.2) | 0.188 | 0.9 (0.5-1.7) | 0.75 |
| | rs35705950 | x | x | 7.9 (5.5-11.3) | $2.1 \times 10^{-29}$ | x | x | 6.1 (3.6-10.2) | $1.0 \times 10^{-11}$ |
| 5 | rs7934606 | 1.7 (1.4-2.2) | $3.8 \times 10^{-6}$ | 1.0 (0.7-1.3) | 0.876 | 1.4 (1.0-2.0) | 0.055 | 0.9 (0.5-1.3) | 0.473 |
| | rs35705950 | x | x | 8.7 (5.8-12.9) | $1.4 \times 10^{-26}$ | x | x | 6.7 (3.8-11.9) | $7.5 \times 10^{-11}$ |
| 6 | rs10902089 | 1.5 (1.2-1.9) | $2.9 \times 10^{-4}$ | 0.9 (0.7-1.2) | 0.69 | 1.5 (1.0-2.1) | 0.031 | 1.0 (0.7-1.6) | 0.813 |
| | rs35705950 | x | x | 8.3 (5.6-12.2) | $1.3 \times 10^{-26}$ | x | x | 6.1 (3.6-10.5) | $6.2 \times 10^{-11}$ |

TABLE 5-continued

Genotypic logistic regression models for the 19 significant SNPs in the screen of lung-expressed gel-forming mucins alone, and after adjusting for rs35705950, in patients with IPF or FIP.

| Model # | SNP | IPF Single SNP Model | | IPF rs35705950 | | FIP Single SNP Model | | FIP rs35705950 | |
|---|---|---|---|---|---|---|---|---|---|
| | | Odds Ratio (95% C.I) | P Value | Odds Ratio (95% C.I) | P Value | Odds Ratio (95% C.I) | P Value | Odds Ratio (95% C.I) | P Value |
| 7 | rs9667239 | 1.9 (1.4-2.7) | $5.6 \times 10^{-5}$ | 0.8 (0.5-1.2) | 0.3 | 2.2 (1.4-3.6) | 0.001 | 1.1 (0.6-2.0) | 0.668 |
| | rs35705950 | x | x | 8.9 (6.0-13.3) | $8.2 \times 10^{-27}$ | x | x | 5.8 (3.3-10.2) | $6.0 \times 10^{-10}$ |
| 8 | rs55846509 | 3.6 (1.7-7.3) | 0.001 | 1.0 (0.5-2.3) | 0.96 | 1.7 (0.6-5.1) | 0.32 | 0.8 (0.3-2.5) | 0.706 |
| | rs35705950 | x | x | 8.3 (5.7-12.1) | $2.7 \times 10^{-28}$ | x | x | 6.4 (3.8-10.7) | $4.8 \times 10^{-12}$ |
| 9 | rs28403537 | 4.6 (2.8-7.6) | $3.2 \times 10^{-9}$ | 1.5 (0.8-2.6) | 0.2 | 2.7 (1.3-5.3) | 0.006 | 0.8 (0.3-1.8) | 0.53 |
| | rs35705950 | x | x | 7.6 (5.2-11.2) | $1.1 \times 10^{-24}$ | x | x | 6.7 (3.8-11.8) | $4.7 \times 10^{-11}$ |
| 10 | MUC5AC-025447 | 1.6 (1.2-2.2) | 0.003 | 1.1 (0.8-1.6) | 0.49 | 1.6 (1.0-2.5) | 0.053 | 1.4 (0.8-2.4) | 0.19 |
| | RS35705950 | x | x | 7.7 (5.3-11.2) | $3.1 \times 10^{-27}$ | x | x | 6.0 (3.5-10.3) | $4.7 \times 10^{-11}$ |
| 11 | rs35288961 | 2.0 (1.5-2.6) | $3.7 \times 10^{-6}$ | 1.1 (0.8-1.5) | 0.58 | 2.2 (1.4-3.5) | $3.2 \times 10^{-4}$ | 1.3 (0.7-2.1) | 0.384 |
| | rs35705950 | x | x | 7.9 (5.4-11.5) | $6.6 \times 10^{-27}$ | x | x | 5.7 (3.3-10.0) | $1.3 \times 10^{-9}$ |
| 12 | rs35671223 | 1.5 (1.2-1.9) | 0.001 | 0.9 (0.7-1.2) | 0.46 | 1.4 (1.0-2.0) | 0.05 | 0.9 (0.6-1.4) | 0.61 |
| | rs35705950 | x | x | 8.5 (5.8-12.4) | $1.1 \times 10^{-28}$ | x | x | 6.3 (3.6-10.9) | $5.4 \times 10^{-11}$ |
| 13 | rs28654232 | 0.6 (0.5-0.8) | $1.1 \times 10^{-4}$ | 0.9 (0.7-1.1) | 0.29 | 0.6 (0.4-0.9) | 0.009 | 0.7 (0.5-1.1) | 0.167 |
| | rs35705950 | x | x | 8.0 (5.5-11.5) | $5.7 \times 10^{-29}$ | x | x | 5.7 (3.4-9.6) | $5.8 \times 10^{-11}$ |
| 14 | rs34595903 | 0.5 (0.4-0.7) | $2.4 \times 10^{-6}$ | 0.8 (0.6-1.1) | 0.116 | 0.5 (0.3-0.7) | 0.001 | 0.6 (0.4-1.0) | 0.041 |
| | rs35705950 | x | x | 7.4 (5.1-10.8) | $7.0 \times 10^{-26}$ | x | x | 5.1 (3.0-8.6) | $1.7 \times 10^{-9}$ |
| 15 | rs2672794 | 0.5 (0.4-0.7) | $1.9 \times 10^{-7}$ | 0.9 (0.7-1.2) | 0.442 | 0.5 (0.3-0.8) | 0.001 | 0.7 (0.4-1.1) | 0.152 |
| | rs35705950 | x | x | 8.0 (5.5-11.6) | $2.5 \times 10^{-27}$ | x | x | 5.5 (3.2-9.3) | $3.2 \times 10^{-10}$ |
| 16 | rs35619543 | 2.1 (1.6-2.8) | $1.5 \times 10^{-8}$ | 1.3 (0.9-1.7) | 0.145 | 2.4 (1.6-3.6) | $3.3 \times 10^{-5}$ | 1.3 (0.8-2.1) | 0.296 |
| | rs35705950 | x | x | 7.6 (5.2-11.2) | $7.0 \times 10^{-25}$ | x | x | 6.1 (3.4-10.9) | $6.8 \times 10^{-10}$ |
| 17 | rs12804004 | 0.6 (0.5-0.8) | $1.2 \times 10^{-4}$ | 0.8 (0.6-1.0) | 0.07 | 0.5 (0.4-0.9) | 0.019 | 0.7 (0.5-1.1) | 0.159 |
| | rs35705950 | x | x | 7.9 (5.5-11.3) | $6.4 \times 10^{-29}$ | x | x | 5.9 (3.5-10.0) | $3.6 \times 10^{-11}$ |
| 18 | rs868903 | 1.6 (1.3-2.1) | $2.8 \times 10^{-5}$ | 1.0 (0.8-1.4) | 0.753 | 1.8 (1.3-2.6) | 0.001 | 1.4 (0.9-2.0) | 0.145 |
| | rs35705950 | x | x | 7.8 (5.3-11.5) | $8.6 \times 10^{-26}$ | x | x | 5.6 (3.2-9.6) | $4.4 \times 10^{-10}$ |

Example 2: Single Nucleotide Polymorphism Rs35705950 Results in Increased Expression of MUC5B Gene The wildtype G allele of the rs35705950 SNP is conserved across primate species. The SNP is directly 5' to a highly conserved region across vertebrate species, and is in the middle of sequence predicted to be involved in MUC5B gene regulation. A bioinformatic analysis of the effect of the rs35705950 SNP predicts a disruption of an E2F binding site and creation of at least two new binding sites (e.g. HOX9 and PAX-2).

Figure 4A:
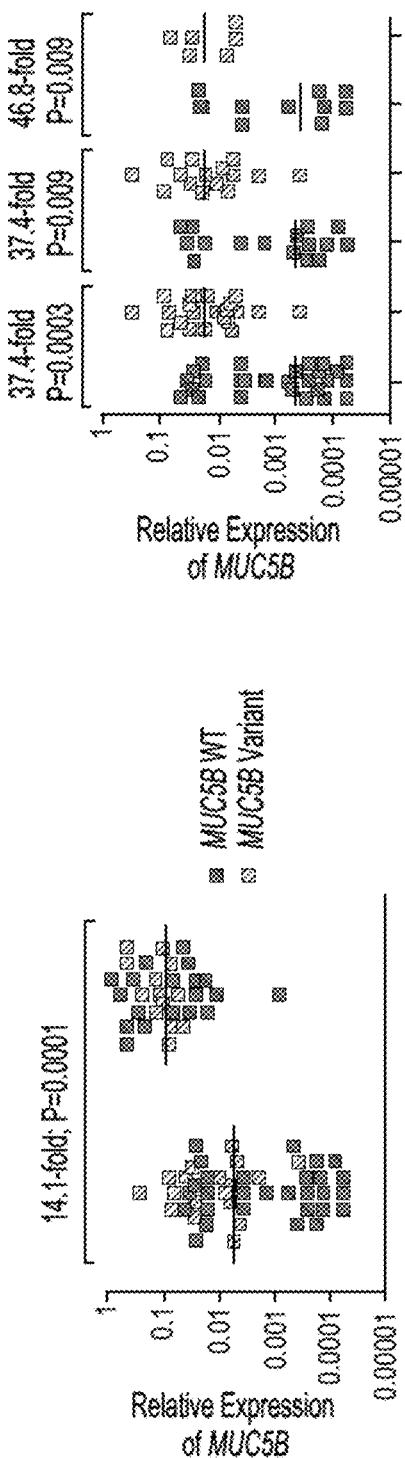
FIGS. 4A-4C represent illustrations of MUC5B gene expression in IPF (N=33) and unaffected subjects (N=47) stratified by MUC5B promoter SNP (rs35705950) genotype and smoking status. A. MUC5B gene expression among unaffected and IPF subjects colored coded based on whether subjects are wildtype (dark grey) or heterozygous for the MUC5B promoter SNP (light grey). B. Comparison of MUC5B expression in unaffected subjects, among unaffected smokers only, and among unaffected non-smokers only, by MUC5B promoter SNP genotype. C. Comparison of MUC5B expression in all IPF subjects, among IPF smokers only, and among IPF non-smokers only, by MUC5B promoter SNP genotype. Lines represent group medians and the expression of MUC5B is determined relative to GAPDH expression
Figure 4B:
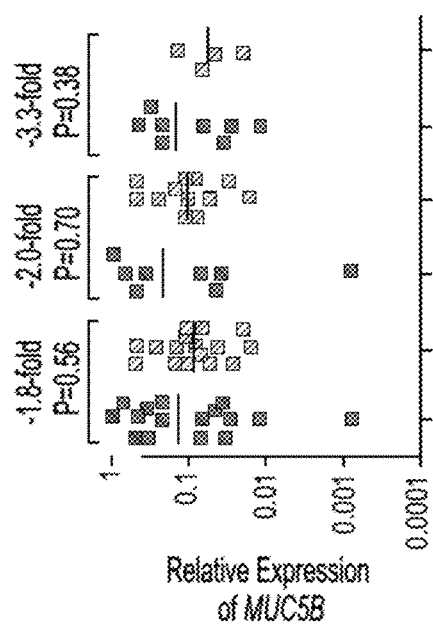
Figure 4C:
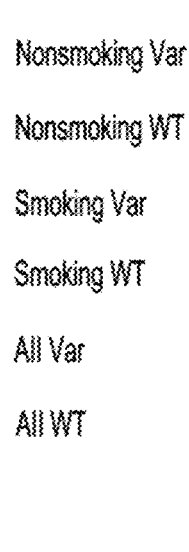

Based on these analyses, the effect of rs35705950 was examined on MUC5B gene expression. In lung tissue from 33 subjects with IPF and 47 unaffected subjects, quantitative RT-PCR revealed that MUC5B gene expression was upregulated 14.1-fold among IPF subjects compared to unaffected subjects (P=0.0001, FIG. 4A). A 37.4-fold increase in MUC5B expression was observed among unaffected subjects carrying at least one copy of the variant allele compared to homozygous wildtype subjects (P=0.0003, FIG. 4B). In contrast, no significant difference in MUC5B gene expression was observed among the IPF subjects with at least one variant allele of rs35705950 (FIG. 4C). Smoking, a potential confounder of MUC5B expression, appeared to have little effect on the association between the rs35705950 variant allele and MUC5B expression among either unaffected or IPF affected subjects (FIGS. 4B and 4C).

Figure 5A:
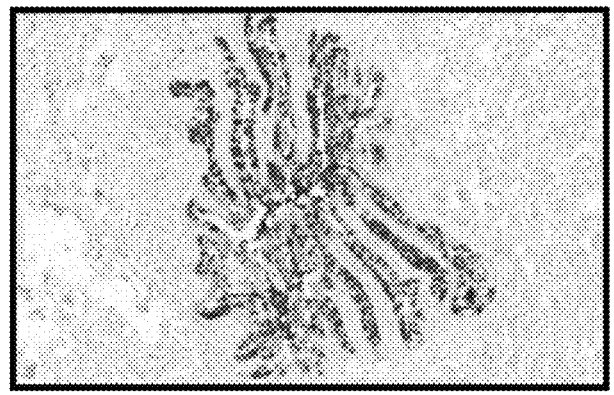
FIGS. 5A-5C represent MUC5B immunohistochemistry of unaffected and IPF tissue. Tissue sections stained for MUC5B distribution in both the unaffected and IPF lung show strong specific cytoplasmic staining within secretory columnar cells of the bronchi and larger proximal bronchioles (FIG. 5A). In subjects with IPF, regions of dense accumulation of MUC5B were observed in areas of microscopic honeycombing and involved patchy staining of the metaplastic epithelia lining the honeycomb cysts (FIG. 5B), as well as the mucus plugs within the cysts (FIG. 5C).
Figure 5B:
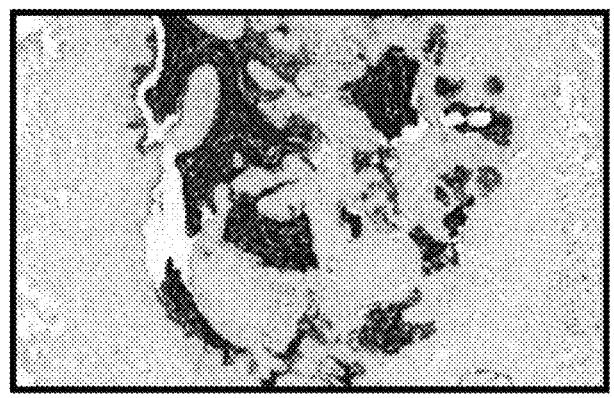
Figure 5C:
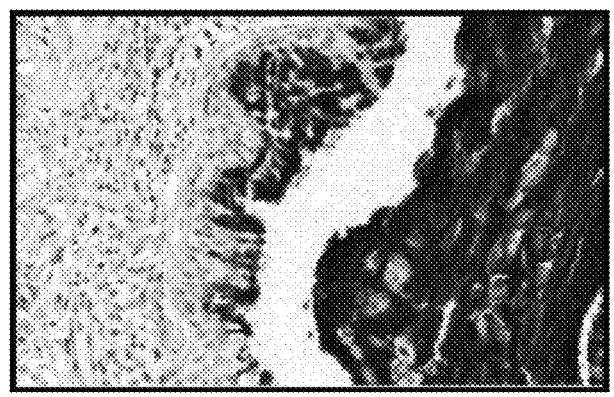

MUC5B immunohistochemical staining in lung tissue showed cytoplasmic staining in secretory columnar cells of the bronchi and larger proximal bronchioles (>200 μm) in IPF cases and controls (FIG. 5A). In subjects with IPF, regions of dense accumulation of MUC5B were observed in areas of microscopic honeycombing and involved patchy staining of the metaplastic epithelia lining the honeycomb cysts (FIG. 5B), as well as the mucous plugs within the cysts (FIG. 5C). No obvious differences were observed in MUC5B staining characteristics in IPF cases with the MUC5B promoter polymorphism.

IPF subjects have significantly more MUC5B lung gene expression than controls, and MUC5B protein is expressed in pathologic lesions of IPF. The present results show that the risk of developing FIP or IPF is substantially correlated with the re35705950 promoter polymorphism, which causes increased MUC5B expression. In aggregate, the data show that MUC5B expression in the lung plays a role in the pathogenesis of pulmonary disease.

Based on the relationship between the SNP and excess production of MUC5B, too much MUC5B can impair mucosal host defense to excessive lung injury from inhaled substances, and, over time, lead to the development of IIP. In addition to the MUC5B promoter SNP, common exposures and basic biological processes can influence either the expression or clearance of MUC5B. For instance, MUC5B expression can be enhanced in the lung by cigarette smoke, acrolein, oxidative stress, IL-6, IL-8, IL-13, IL-17, 17β-estradiol, extracellular nucleotides, or epigenetic changes that alter DNA methylation or chromatin structure. Moreover, clearance of lung mucus is dependent on effective ciliary motion, adequate hydration of the periciliary liquid layer, and an intact cough. Regardless of the cause, the present results indicate that excess MUC5B can compromise mucosal host defense, reducing lung clearance of inhaled particles, dissolved chemicals, and microorganisms. Given the importance of environmental exposures, such as asbestos, silica, and other pollutants in the development of other forms of interstitial lung disease, it is logical to speculate that common inhaled particles, such as those associated with cigarette smoke or air pollution, might lead to or contribute to exaggerated interstitial injury in individuals who have defects in mucosal host defense.

In addition, excess MUC5B in the respiratory bronchioles can interfere with alveolar repair. Alveolar injury can lead to collapse of bronchoalveolar units and this focal lung injury is repaired through re-epithelialization of the alveolus by type II alveolar epithelial cells. Thus, MUC5B can impede alveolar repair by either interfering with the interaction between the type II alveolar epithelial cells and the underlying matrix, or by interfering with the surface tension properties of surfactant. Either failure to re-epithelialize the basal lamina of the alveolus or suboptimal surfactant biology could enhance ongoing collapse and fibrosis of adjacent bronchoalveolar units, and eventually result in IIP.

Lesions of IPF are spatially heterogeneous, suggesting that IPF is multifocal, originating in individual bronchoalveolar units. Since SNP rs35705950 occurs in the promoter region of MUC5B and is predicted to disrupt transcription factor binding sites, ectopic production of MUC5B in cells or locations that cause injury to the bronchoalveolar unit can be a causative agent. Unscreened genetic variants (especially in the inaccessible repetitive mucin regions) may be in linkage disequilibrium with the MUC5B promoter SNP and affect the function of other lung mucins.

The present observations provide a novel clinical approach to pulmonary disorders such as IIP. Invoking secreted airway mucins in the pathogenesis of pulmonary fibrosis suggests that the airspace plays a role in the pathogenesis of IIP. While the SNP (rs35705950) in the MUC5B promoter can be used to identify individuals at risk for developing IP, the observation that mucin biology is be important in the etiology of UP reorients the focus of pathogenic and therapeutic studies in interstitial lung disease to lung mucins and the airspace. Moreover, the genetic causes of IIP (e.g., MUC5B, surfactant protein C, surfactant protein A2, and the two telomerase genes TERC and TERT) provide insight into the unique clinical manifestations of this complex disease process, and consequently, lead to earlier detection, more predictable prognosis, and personalized therapeutic strategies.

Example 3: Genetic Variant MUC5B Associated with Attenuated Form of Pulmonary Disease The data described herein demonstrate that the genetic variant MUC5B rs35705950 is associated with development of pulmonary disease. We next examined whether rs35705950 genetic variant is associated with disease severity and prognosis. We found that homozygous wildtype subjects (GG), i.e., those having normal MUC5B gene sequence, displayed a steeper decline in forced vital capacity (FVC) over time as compared to subjects with at least one T allele (P=0.0006). Essentially, while FVC declines for both groups, the decline is more gradual in those carrying the G→T polymorphism. For GG subjects, the FVC absolute value fell from about 3.4 liters to about 3.1 liters over years 1-3 of the study. For GT and TT subjects, the FVC absolute value still fell, but started at over 3.5 liters and fell to about 3.4 liters over years 1-3 of the study.

Additionally, we observed an association between death with subjects having at least one T allele having a lower mortality (OR(95% CI)=0.37(0.20–0.67); p=0.001) after adjusting for gender, history of smoking and DLCO (diffusion lung capacity for CO2). We also observed an association with time to death and the T allele; Hazard ratio (95% CI) 0.50(0.30–0.83) p=0.0069 after adjustment for gender, history of smoking and DLCO. These results suggest that in addition to being a strong risk factor for pulmonary disease development, the rs35705950 SNP can indicate a less severe prognosis for the pulmonary disease.

What is claimed is:

1. A method of detecting a genetic variant MUC2 gene in a human subject having a pulmonary fibrotic condition, the method comprising:
   (i) obtaining a biological sample from a human subject having a pulmonary fibrotic condition, and
   (ii) detecting whether a genetic variant MUC2 gene sequence is present in said biological sample, wherein said detecting comprises detecting an A allele at single nucleotide polymorphism (SNP) rs41480348 of said genetic variant MUC2 gene sequence.

2. The method of claim 1, further comprising detecting the minor allele of SNP rs41453346, rs7127117, rs10902081, rs7934606, or rs10902089.

3. The method of claim 1, wherein said pulmonary fibrotic condition is idiopathic pulmonary fibrosis (IPF) or familial interstitial pneumonia (FIP).

4. The method of claim 1, wherein said biological sample is a pulmonary tissue or a bodily fluid.

5. The method of claim 1, wherein said detecting comprises hybridization with a labeled nucleic acid probe.

6. The method of claim 5, wherein said genetic variant MUC2 gene sequence is in a detection device capable of indicating hybridization of said labeled nucleic acid probe to said SNP rs41480348 of said genetic variant MUC2 gene sequence.

7. The method of claim 5, further comprising administering to said human subject an effective amount of an anti-inflammatory agent when binding of said labeled nucleic acid probe to said SNP rs41480348 of said genetic variant MUC2 gene sequence is detected in said sample of said human subject in step (ii).

8. The method of claim 1, wherein said labeled nucleic acid probe has at least 10 nucleotides.

9. The method of claim 1, wherein said genetic variant MUC2 gene sequence is extracted from said biological sample.

10. The method of claim 1, wherein said genetic variant MUC2 gene sequence is an amplification product of a genetic variant MUC2 gene.

11. A method of treating a pulmonary fibrotic condition in a human subject in need thereof, the method comprising:
    (i) obtaining a biological sample from a human subject with a pulmonary fibrotic condition;
    (ii) detecting whether a genetic variant MUC2 gene sequence is present in said biological sample, wherein said detecting comprises detecting an A allele at single nucleotide polymorphism (SNP) rs41480348 of said genetic variant MUC2 gene sequence, and
    (iii) administering to said human subject an effective amount of an anti-inflammatory agent when said A allele at SNP rs41480348 of said genetic variant MUC2 gene sequence is detected in said sample of said human subject in step (ii).

12. The method of claim 11, further comprising detecting the minor allele of SNP, rs41453346, rs7127117, rs10902081, rs7934606, or rs10902089.

13. The method of claim 11, wherein said pulmonary fibrotic condition is idiopathic pulmonary fibrosis (IPF) or familial interstitial pneumonia (FIP).

14. The method of claim 11, wherein said biological sample is a pulmonary tissue or a bodily fluid.

15. The method of claim 11, wherein said detecting comprises hybridization with a labeled nucleic acid probe.

16. The method of claim 15, wherein said labeled nucleic acid probe has at least 10 nucleotides.

17. The method of claim 11, wherein said genetic variant MUC2 gene sequence is extracted from said biological sample.

18. The method of claim 11, wherein said genetic variant MUC2 gene sequence is an amplification product of a genetic variant MUC2 gene.

19. The method of claim 15, wherein said genetic variant MUC2 gene sequence is in a detection device capable of indicating hybridization of said labeled nucleic acid probe to said SNP rs41480348 of said genetic variant MUC2 gene sequence.

* * * * *

SEQUENCE LISTING

```
<160> NUMBER OF SEQ ID NOS: 53

<210> SEQ ID NO 1
<211> LENGTH: 24
<212> TYPE: DNA
<213> ORGANISM: Artificial Sequence
<220> FEATURE:
<223> OTHER INFORMATION: Synthetic polynucleotide DNA forward primer

<400> SEQUENCE: 1
ggttctcctt gtcttgcagc ccct                                          24

<210> SEQ ID NO 2
<211> LENGTH: 23
<212> TYPE: DNA
<213> ORGANISM: Artificial Sequence
<220> FEATURE:
<223> OTHER INFORMATION: Synthetic polynucleotide DNA reverse primer

<400> SEQUENCE: 2
atgggctctt ggtctgctca gag                                           23

<210> SEQ ID NO 3
<211> LENGTH: 25
<212> TYPE: DNA
<213> ORGANISM: Artificial Sequence
<220> FEATURE:
<223> OTHER INFORMATION: Synthetic polynucleotide DNA forward primer
```

```
<400> SEQUENCE: 3
gggcctggct ctgagtacac atcct                                          25

<210> SEQ ID NO 4
<211> LENGTH: 24
<212> TYPE: DNA
<213> ORGANISM: Artificial Sequence
<220> FEATURE:
<223> OTHER INFORMATION: Synthetic polynucleotide DNA reverse primer

<400> SEQUENCE: 4
aaggaaaggg acacagccgg ttcc                                           24

<210> SEQ ID NO 5
<211> LENGTH: 23
<212> TYPE: DNA
<213> ORGANISM: Artificial Sequence
<220> FEATURE:
<223> OTHER INFORMATION: Synthetic polynucleotide DNA forward primer

<400> SEQUENCE: 5
gggtccccat tcatggcagg att                                            23

<210> SEQ ID NO 6
<211> LENGTH: 24
<212> TYPE: DNA
<213> ORGANISM: Artificial Sequence
<220> FEATURE:
<223> OTHER INFORMATION: Synthetic polynucleotide DNA reverse primer

<400> SEQUENCE: 6
tttctccatg gcagagctgg gacc                                           24

<210> SEQ ID NO 7
<211> LENGTH: 25
<212> TYPE: DNA
<213> ORGANISM: Artificial Sequence
<220> FEATURE:
<223> OTHER INFORMATION: Synthetic polynucleotide DNA forward primer

<400> SEQUENCE: 7
ctagtgggag ggacgagggc aaagt                                          25

<210> SEQ ID NO 8
<211> LENGTH: 23
<212> TYPE: DNA
<213> ORGANISM: Artificial Sequence
<220> FEATURE:
<223> OTHER INFORMATION: Synthetic polynucleotide DNA reverse primer

<400> SEQUENCE: 8
ctcgtggctg tgactgcacc cag                                            23

<210> SEQ ID NO 9
<211> LENGTH: 20
<212> TYPE: DNA
<213> ORGANISM: Artificial Sequence
<220> FEATURE:
<223> OTHER INFORMATION: Synthetic polynucleotide DNA forward primer

<400> SEQUENCE: 9
ttggctaagg tgggagacct                                                20

<210> SEQ ID NO 10
<211> LENGTH: 20
```

```
<212> TYPE: DNA
<213> ORGANISM: Artificial Sequence
<220> FEATURE:
<223> OTHER INFORMATION: Synthetic polynucleotide DNA reverse primer

<400> SEQUENCE: 10
agcttgggaa tgtgagaacg                                           20

<210> SEQ ID NO 11
<211> LENGTH: 23
<212> TYPE: DNA
<213> ORGANISM: Artificial Sequence
<220> FEATURE:
<223> OTHER INFORMATION: Synthetic polynucleotide DNA forward primer

<400> SEQUENCE: 11
catgaggggt gacaggtggc aaa                                       23

<210> SEQ ID NO 12
<211> LENGTH: 23
<212> TYPE: DNA
<213> ORGANISM: Artificial Sequence
<220> FEATURE:
<223> OTHER INFORMATION: Synthetic polynucleotide DNA reverse primer

<400> SEQUENCE: 12
cccgcgtttg tctttctgaa gtt                                       23

<210> SEQ ID NO 13
<211> LENGTH: 23
<212> TYPE: DNA
<213> ORGANISM: Artificial Sequence
<220> FEATURE:
<223> OTHER INFORMATION: Synthetic polynucleotide DNA forward primer

<400> SEQUENCE: 13
ggtcagaagc tttgaagatg ggc                                       23

<210> SEQ ID NO 14
<211> LENGTH: 23
<212> TYPE: DNA
<213> ORGANISM: Artificial Sequence
<220> FEATURE:
<223> OTHER INFORMATION: Synthetic polynucleotide DNA reverse primer

<400> SEQUENCE: 14
cttgtccaat gccagccctg atc                                       23

<210> SEQ ID NO 15
<211> LENGTH: 20
<212> TYPE: DNA
<213> ORGANISM: Artificial Sequence
<220> FEATURE:
<223> OTHER INFORMATION: Synthetic polynucleotide DNA forward primer

<400> SEQUENCE: 15
ctgccagggt taatgaggag                                           20

<210> SEQ ID NO 16
<211> LENGTH: 20
<212> TYPE: DNA
<213> ORGANISM: Artificial Sequence
<220> FEATURE:
<223> OTHER INFORMATION: Synthetic polynucleotide DNA reverse primer

<400> SEQUENCE: 16
```
ggatcaggaa ggatttgcag                                                      20

<210> SEQ ID NO 17
<211> LENGTH: 24
<212> TYPE: DNA
<213> ORGANISM: Artificial Sequence
<220> FEATURE:
<223> OTHER INFORMATION: Synthetic polynucleotide DNA forward primer

<400> SEQUENCE: 17
aggcaggctg gctgaccact gttt                                                 24

<210> SEQ ID NO 18
<211> LENGTH: 23
<212> TYPE: DNA
<213> ORGANISM: Artificial Sequence
<220> FEATURE:
<223> OTHER INFORMATION: Synthetic polynucleotide DNA reverse primer

<400> SEQUENCE: 18
cgtgaagaca gcatcgagag ggg                                                  23

<210> SEQ ID NO 19
<211> LENGTH: 20
<212> TYPE: DNA
<213> ORGANISM: Artificial Sequence
<220> FEATURE:
<223> OTHER INFORMATION: Synthetic polynucleotide DNA forward primer

<400> SEQUENCE: 19
ttggctaagg tgggagacct                                                      20

<210> SEQ ID NO 20
<211> LENGTH: 51
<212> TYPE: DNA
<213> ORGANISM: Artificial Sequence
<220> FEATURE:
<223> OTHER INFORMATION: Synthetic polynucleotide DNA of SNP identified
      in resequencing of the MUC5B promoter

<400> SEQUENCE: 20
gtcacctgcc caggtccccg aggccyggaa caccttcctg ctgggcccac c                   51

<210> SEQ ID NO 21
<211> LENGTH: 52
<212> TYPE: DNA
<213> ORGANISM: Artificial Sequence
<220> FEATURE:
<223> OTHER INFORMATION: Synthetic polynucleotide DNA of SNP identified
      in resequencing of the MUC5B promoter

<400> SEQUENCE: 21 ccacccagg agttgggggg cccccgtrcc agggagcagg aggctgccga gg                   52

<210> SEQ ID NO 22
<211> LENGTH: 51
<212> TYPE: DNA
<213> ORGANISM: Artificial Sequence
<220> FEATURE:
<223> OTHER INFORMATION: Synthetic polynucleotide DNA of SNP identified
      in resequencing of the MUC5B promoter

<400> SEQUENCE: 22
gtggccctga tcactggtgc ctggayggcc tctgaagggg tctgtggggt c                   51

<210> SEQ ID NO 23

```
<211> LENGTH: 51
<212> TYPE: DNA
<213> ORGANISM: Artificial Sequence
<220> FEATURE:
<223> OTHER INFORMATION: Synthetic polynucleotide DNA of SNP identified
      in resequencing of the MUC5B promoter

<400> SEQUENCE: 23 aaccccctc gggttctgtg tggtcyaggc cgcccctttg tctccactgc c             51

<210> SEQ ID NO 24
<211> LENGTH: 49
<212> TYPE: DNA
<213> ORGANISM: Artificial Sequence
<220> FEATURE:
<223> OTHER INFORMATION: Synthetic polynucleotide DNA of SNP identified
      in resequencing of the MUC5B promoter

<400> SEQUENCE: 24
tttcttcctt tatcttctgt tttcagckcc ttcaactgtg aagaagtga               49

<210> SEQ ID NO 25
<211> LENGTH: 50
<212> TYPE: DNA
<213> ORGANISM: Artificial Sequence
<220> FEATURE:
<223> OTHER INFORMATION: Synthetic polynucleotide DNA of SNP identified
      in resequencing of the MUC5B promoter

<400> SEQUENCE: 25
tgccccggac ccagcccagt tcccartggg ccctctgccc ggggaggtgc              50

<210> SEQ ID NO 26
<211> LENGTH: 55
<212> TYPE: DNA
<213> ORGANISM: Artificial Sequence
<220> FEATURE:
<223> OTHER INFORMATION: Synthetic polynucleotide DNA of SNP identified
      in resequencing of the MUC5B promoter

<400> SEQUENCE: 26
ggtgggcatc ggcttgtgag ctggagccgy gggcagggag ggggatgtc acgag         55

<210> SEQ ID NO 27
<211> LENGTH: 54
<212> TYPE: DNA
<213> ORGANISM: Artificial Sequence
<220> FEATURE:
<223> OTHER INFORMATION: Synthetic polynucleotide DNA of SNP identified
      in resequencing of the MUC5B promoter

<400> SEQUENCE: 27
ggctaaggtg ggagacctgg gcgggtgcrt cgggggacg tctgcagcag aggc          54

<210> SEQ ID NO 28
<211> LENGTH: 58
<212> TYPE: DNA
<213> ORGANISM: Artificial Sequence
<220> FEATURE:
<223> OTHER INFORMATION: Synthetic polynucleotide DNA of SNP identified
      in resequencing of the MUC5B promoter

<400> SEQUENCE: 28
tgcgtcgggg ggacgtctgc agcagaggcc ygggcagcag gcacacccct cctgccag     58

<210> SEQ ID NO 29
<211> LENGTH: 50
```

```
<212> TYPE: DNA
<213> ORGANISM: Artificial Sequence
<220> FEATURE:
<223> OTHER INFORMATION: Synthetic polynucleotide DNA of SNP identified
      in resequencing of the MUC5B promoter

<400> SEQUENCE: 29
ggggcctggg tgcagtcaca gccacragcc caggggtggg gactctggcc             50

<210> SEQ ID NO 30
<211> LENGTH: 50
<212> TYPE: DNA
<213> ORGANISM: Artificial Sequence
<220> FEATURE:
<223> OTHER INFORMATION: Synthetic polynucleotide DNA of SNP identified
      in resequencing of the MUC5B promoter

<400> SEQUENCE: 30
cccctcccac cgtgccgtgc tgcagygggt ctaccggcct ggatgtgaaa             50

<210> SEQ ID NO 31
<211> LENGTH: 50
<212> TYPE: DNA
<213> ORGANISM: Artificial Sequence
<220> FEATURE:
<223> OTHER INFORMATION: Synthetic polynucleotide DNA of SNP identified
      in resequencing of the MUC5B promoter

<400> SEQUENCE: 31
ccgtgccgtg ctgcagcggg tctacyggcc tggatgtgaa agagagcttg             50

<210> SEQ ID NO 32
<211> LENGTH: 50
<212> TYPE: DNA
<213> ORGANISM: Artificial Sequence
<220> FEATURE:
<223> OTHER INFORMATION: Synthetic polynucleotide DNA of SNP identified
      in resequencing of the MUC5B promoter

<400> SEQUENCE: 32
agtcccggaa gtgagcgggg agctaygctg agatctggga gacccctgc              50

<210> SEQ ID NO 33
<211> LENGTH: 50
<212> TYPE: DNA
<213> ORGANISM: Artificial Sequence
<220> FEATURE:
<223> OTHER INFORMATION: Synthetic polynucleotide DNA of SNP identified
      in resequencing of the MUC5B promoter

<400> SEQUENCE: 33
gggagctacg ctgagatctg ggagaycccc tgcccccacc caggtacagg             50

<210> SEQ ID NO 34
<211> LENGTH: 50
<212> TYPE: DNA
<213> ORGANISM: Artificial Sequence
<220> FEATURE:
<223> OTHER INFORMATION: Synthetic polynucleotide DNA of SNP identified
      in resequencing of the MUC5B promoter

<400> SEQUENCE: 34
tacgctgaga tctgggagac cccctkcccc cacccaggta cagggccagg             50

<210> SEQ ID NO 35
<211> LENGTH: 50
<212> TYPE: DNA
```

```
<213> ORGANISM: Artificial Sequence
<220> FEATURE:
<223> OTHER INFORMATION: Synthetic polynucleotide DNA of SNP identified
      in resequencing of the MUC5B promoter

<400> SEQUENCE: 35
gcagaagccc gaggtgtgcc ctgagktaaa gaaaccgtca caaagaacaa              50

<210> SEQ ID NO 36
<211> LENGTH: 50
<212> TYPE: DNA
<213> ORGANISM: Artificial Sequence
<220> FEATURE:
<223> OTHER INFORMATION: Synthetic polynucleotide DNA of SNP identified
      in resequencing of the MUC5B promoter

<400> SEQUENCE: 36
tgtctccgcc ctccatctcc agaacrttct cacattccca agctgaaacc              50

<210> SEQ ID NO 37
<211> LENGTH: 52
<212> TYPE: DNA
<213> ORGANISM: Artificial Sequence
<220> FEATURE:
<223> OTHER INFORMATION: Synthetic polynucleotide DNA of SNP identified
      in resequencing of the MUC5B promoter

<400> SEQUENCE: 37
cccaagctga aaccctgtcc ccatgmaaca ccagctcacc atccctctg cc            52

<210> SEQ ID NO 38
<211> LENGTH: 52
<212> TYPE: DNA
<213> ORGANISM: Artificial Sequence
<220> FEATURE:
<223> OTHER INFORMATION: Synthetic polynucleotide DNA of SNP identified
      in resequencing of the MUC5B promoter

<400> SEQUENCE: 38
ggcgcccacc gtccacactc cgtctytgcg ggtttcatga ctccaggggc ag           52

<210> SEQ ID NO 39
<211> LENGTH: 51
<212> TYPE: DNA
<213> ORGANISM: Artificial Sequence
<220> FEATURE:
<223> OTHER INFORMATION: Synthetic polynucleotide DNA of SNP identified
      in resequencing of the MUC5B promoter

<400> SEQUENCE: 39
tttcatgact ccaggggcag cacacragtg gcccctcctg cctttgtcct c            51

<210> SEQ ID NO 40
<211> LENGTH: 51
<212> TYPE: DNA
<213> ORGANISM: Artificial Sequence
<220> FEATURE:
<223> OTHER INFORMATION: Synthetic polynucleotide DNA of SNP identified
      in resequencing of the MUC5B promoter

<400> SEQUENCE: 40
ctccaggggc agcacacgag tggccyctcc tgcctttgtc tctgtgtcc a             51

<210> SEQ ID NO 41
<211> LENGTH: 51
<212> TYPE: DNA
<213> ORGANISM: Artificial Sequence
```

<220> FEATURE:
<223> OTHER INFORMATION: Synthetic polynucleotide DNA of SNP identified in resequencing of the MUC5B promoter

<400> SEQUENCE: 41
cccccatgga gcagcctggg ccagccyctc cttttcacgg ctgaaccgta t    51

<210> SEQ ID NO 42
<211> LENGTH: 53
<212> TYPE: DNA
<213> ORGANISM: Artificial Sequence
<220> FEATURE:
<223> OTHER INFORMATION: Synthetic polynucleotide DNA of SNP identified in resequencing of the MUC5B promoter

<400> SEQUENCE: 42
acccccacca gcagggcaca gggctccrgg tccccacgtc tctgccaaca ctt    53

<210> SEQ ID NO 43
<211> LENGTH: 50
<212> TYPE: DNA
<213> ORGANISM: Artificial Sequence
<220> FEATURE:
<223> OTHER INFORMATION: Synthetic polynucleotide DNA of SNP identified in resequencing of the MUC5B promoter

<400> SEQUENCE: 43
cttgatcccc gccatcctat tgagcrtgag acaggtcaga agctttgaag    50

<210> SEQ ID NO 44
<211> LENGTH: 50
<212> TYPE: DNA
<213> ORGANISM: Artificial Sequence
<220> FEATURE:
<223> OTHER INFORMATION: Synthetic polynucleotide DNA of SNP identified in resequencing of the MUC5B promoter

<400> SEQUENCE: 44
gtctgcgcca cggagcattc aggacrctgg tgaccaggga gccaggaggt    50

<210> SEQ ID NO 45
<211> LENGTH: 54
<212> TYPE: DNA
<213> ORGANISM: Artificial Sequence
<220> FEATURE:
<223> OTHER INFORMATION: Synthetic polynucleotide DNA of SNP identified in resequencing of the MUC5B promoter

<400> SEQUENCE: 45
cgtcaaggag gtttaccaca tagccccrg gaagcccacc cgacaccagc cgga    54

<210> SEQ ID NO 46
<211> LENGTH: 56
<212> TYPE: DNA
<213> ORGANISM: Artificial Sequence
<220> FEATURE:
<223> OTHER INFORMATION: Synthetic polynucleotide DNA of SNP identified in resequencing of the MUC5B promoter

<400> SEQUENCE: 46
tttaccacat agccccrgg aagcccaccc racaccagcc ggaggtgcta ggcttc    56

<210> SEQ ID NO 47
<211> LENGTH: 50
<212> TYPE: DNA
<213> ORGANISM: Artificial Sequence
<220> FEATURE:

<223> OTHER INFORMATION: Synthetic polynucleotide DNA of SNP identified
      in resequencing of the MUC5B promoter

<400> SEQUENCE: 47
cccacccgac accagccgga ggtgcyaggc ttctgcggct cccacctggg         50

<210> SEQ ID NO 48
<211> LENGTH: 51
<212> TYPE: DNA
<213> ORGANISM: Artificial Sequence
<220> FEATURE:
<223> OTHER INFORMATION: Synthetic polynucleotide DNA of SNP identified
      in resequencing of the MUC5B promoter

<400> SEQUENCE: 48
ggacccatgg tcagtggctg ggggtrctgc ccagaggctg ggattccctt c       51

<210> SEQ ID NO 49
<211> LENGTH: 51
<212> TYPE: DNA
<213> ORGANISM: Artificial Sequence
<220> FEATURE:
<223> OTHER INFORMATION: Synthetic polynucleotide DNA of SNP identified
      in resequencing of the MUC5B promoter

<400> SEQUENCE: 49
gccatctagg acgggtgcca ggtggrgtag gcccttctct cccttccgat t       51

<210> SEQ ID NO 50
<211> LENGTH: 51
<212> TYPE: DNA
<213> ORGANISM: Artificial Sequence
<220> FEATURE:
<223> OTHER INFORMATION: Synthetic polynucleotide DNA of SNP identified
      in resequencing of the MUC5B promoter

<400> SEQUENCE: 50
ggtggggtag gcccttctct cccttscgat tctcagaagc tgctgggggt g       51

<210> SEQ ID NO 51
<211> LENGTH: 53
<212> TYPE: DNA
<213> ORGANISM: Artificial Sequence
<220> FEATURE:
<223> OTHER INFORMATION: Synthetic polynucleotide DNA of SNP identified
      in resequencing of the MUC5B promoter

<400> SEQUENCE: 51
agcccctccc cgagagcaaa cacacrtggc tggagcgggg aagagcatgg tgc     53

<210> SEQ ID NO 52
<211> LENGTH: 51
<212> TYPE: DNA
<213> ORGANISM: Artificial Sequence
<220> FEATURE:
<223> OTHER INFORMATION: Synthetic polynucleotide DNA of SNP identified
      in resequencing of the MUC5B promoter

<400> SEQUENCE: 52
cacgtggctg gagcggggaa gagcayggtg ccctgcgtgg cctggcctgg c       51

<210> SEQ ID NO 53
<211> LENGTH: 50
<212> TYPE: DNA
<213> ORGANISM: Artificial Sequence
<220> FEATURE:
<223> OTHER INFORMATION: Synthetic polynucleotide DNA of SNP identified

```
in resequencing of the MUC5B promoter

<400> SEQUENCE: 53
gccgcaggca ggtaagagcc ccccaytccg ccccctctcg atgctgtctt         50
```